(12) United States Patent
Sandler et al.

(10) Patent No.: US 10,694,948 B2
(45) Date of Patent: Jun. 30, 2020

(54) METHODS OF EXOSKELETON COMMUNICATION AND CONTROL

(71) Applicant: Ekso Bionics, Inc., Richmond, CA (US)

(72) Inventors: Reuben Sandler, Underwood, WA (US); Katherine Strausser, Berkeley, CA (US); Mark Fiedler, Berkeley, CA (US); Kurt Amundson, Berkeley, CA (US); Dan Brown, Pleasanton, CA (US); Renata Smith, Berkeley, CA (US); Matthew D Sweeney, Sacramento, CA (US); Russdon Angold, American Canyon, CA (US); Niel McCaffrey, Mill Valley, CA (US); Duane Edmonds, Oakland, CA (US); Chris Meadows, Richmond, CA (US); Jared Jones, Oakland, CA (US); Kelly Mettler, Richmond, CA (US)

(73) Assignee: EKSO BIONICS, Richmond, CA (US)

( * ) Notice: Subject to any disclaimer, the term of this patent is extended or adjusted under 35 U.S.C. 154(b) by 355 days.

(21) Appl. No.: 15/566,146

(22) PCT Filed: Apr. 14, 2016

(86) PCT No.: PCT/US2016/027536
§ 371 (c)(1),
(2) Date: Oct. 12, 2017

(87) PCT Pub. No.: WO2016/168463
PCT Pub. Date: Oct. 20, 2016

(65) Prior Publication Data
US 2018/0092536 A1 Apr. 5, 2018

Related U.S. Application Data

(60) Provisional application No. 62/147,076, filed on Apr. 14, 2015, provisional application No. 62/248,659, filed on Oct. 30, 2015.

(51) Int. Cl.
*A61B 5/00* (2006.01)
*A61H 3/00* (2006.01)
(Continued)

(52) U.S. Cl.
CPC ............ *A61B 5/0024* (2013.01); *A61B 5/112* (2013.01); *A61B 5/1116* (2013.01); *A61B 5/224* (2013.01);
(Continued)

(58) Field of Classification Search
CPC ............ A61B 5/00; A61H 3/00; G08C 17/00
See application file for complete search history.

(56) References Cited

U.S. PATENT DOCUMENTS

| 4,697,808 A | 10/1987 | Larson et al. |
| 7,010,390 B2 | 3/2006 | Graf et al. |

(Continued)

FOREIGN PATENT DOCUMENTS

| CN | 103876756 | 6/2014 |
| WO | 2014/159577 | 10/2014 |

OTHER PUBLICATIONS

Manteuffel, D, "Characteristic Mode based antenna design—A straight forward approach to small form factor antenna integration," 2015 9th European Conference on Antennas and Propagation (EuCAP), 2015, pp. 1-5, found at: http://ieeexplore.ieee.org/xpl/login.jsp?tp=&arnumber=7229004&url=http%3A%2F%2Fieeexplore.ieee.org%2Fiel7%2F7209133%2F7228134%2F07229004.pdf%3Farnumber%3D7229004.

*Primary Examiner* — Kira Nguyen
(74) *Attorney, Agent, or Firm* — Diederiks & Whitelaw, PLC

(57) ABSTRACT

A first exoskeleton is in communication with a central server or a peripheral device. The first exoskeleton collects first data and transmits the first data to the central server or
(Continued)

peripheral device. The central server or peripheral device generates second data using the first data and transmits the second data to the first exoskeleton or a second exoskeleton.

20 Claims, 16 Drawing Sheets

(51) Int. Cl.
   *G08C 17/00* (2006.01)
   *A61H 1/02* (2006.01)
   *A61B 5/11* (2006.01)
   *A61B 5/22* (2006.01)
   *G08C 17/02* (2006.01)
   *A61H 3/02* (2006.01)
   *A61H 3/04* (2006.01)
   *A61B 5/0402* (2006.01)
   *A61B 5/145* (2006.01)
   *A61B 5/0476* (2006.01)
   *A61B 5/01* (2006.01)

(52) U.S. Cl.
   CPC ........... *A61B 5/486* (2013.01); *A61H 1/0255* (2013.01); *A61H 3/00* (2013.01); *G08C 17/00* (2013.01); *G08C 17/02* (2013.01); *A61B 5/01* (2013.01); *A61B 5/0402* (2013.01); *A61B 5/0476* (2013.01); *A61B 5/1112* (2013.01); *A61B 5/1117* (2013.01); *A61B 5/14532* (2013.01); *A61B 2505/09* (2013.01); *A61B 2562/0247* (2013.01); *A61H 3/02* (2013.01); *A61H 3/04* (2013.01); *A61H 2201/165* (2013.01); *A61H 2201/1676* (2013.01); *A61H 2201/501* (2013.01); *A61H 2201/5012* (2013.01); *A61H 2201/5043* (2013.01); *A61H 2201/5058* (2013.01); *A61H 2201/5064* (2013.01); *A61H 2201/5084* (2013.01); *A61H 2201/5097* (2013.01); *A61H 2230/04* (2013.01); *A61H 2230/06* (2013.01); *A61H 2230/202* (2013.01); *A61H 2230/25* (2013.01); *A61H 2230/30* (2013.01); *A61H 2230/60* (2013.01)

(56) References Cited

U.S. PATENT DOCUMENTS

| | | |
|---|---|---|
| 7,031,837 B1 | 4/2006 | Foust |
| 7,117,067 B2 | 10/2006 | McLurkin et al. |
| 7,901,368 B2 | 3/2011 | Flaherty et al. |
| 8,655,537 B2 | 2/2014 | Ferguson et al. |
| 8,905,925 B2 | 12/2014 | Beck et al. |
| 9,158,376 B2 | 10/2015 | Kazerooni et al. |
| 9,775,763 B2 | 10/2017 | Aleksov et al. |
| 2006/0184280 A1 | 8/2006 | Oddsson et al. |
| 2010/0198124 A1 | 8/2010 | Bhugra |
| 2010/0204867 A1 | 8/2010 | Longstaff |
| 2011/0246123 A1 | 10/2011 | Dellostritto et al. |
| 2012/0259430 A1* | 10/2012 | Han .................... A61F 2/60  623/24 |
| 2013/0158445 A1* | 6/2013 | Kazerooni ............ A61H 3/00  601/35 |
| 2014/0100491 A1 | 4/2014 | Hu et al. |
| 2014/0171838 A1* | 6/2014 | Aleksov ............. A61H 1/0244  601/33 |
| 2015/0051519 A1 | 2/2015 | Morbi et al. |
| 2015/0100135 A1* | 4/2015 | Ives .................... A61B 5/6828  623/25 |
| 2015/0141878 A1 | 5/2015 | Roy et al. |
| 2015/0289995 A1* | 10/2015 | Wilkinson .......... B25J 19/0091  623/27 |
| 2015/0309316 A1 | 10/2015 | Osterhout et al. |
| 2016/0030272 A1 | 2/2016 | Angold et al. |

\* cited by examiner

METHODS OF EXOSKELETON COMMUNICATION AND CONTROL

CROSS REFERENCE TO RELATED APPLICATIONS

This application represents a National Stage application of PCT/US2016/027536 filed Apr. 14, 2017 and titled "Methods of Exoskeleton Communication and Control", which claims the benefit of U.S. Provisional Patent Application Ser. No. 62/147,076, which was filed on Apr. 14, 2015 and titled "Methods and Devices for Improving the Functionality of a Powered Human Exoskeleton Device Equipped with a Data Link", and U.S. Provisional Patent Application Ser. No. 62/248,659, which was filed on Oct. 30, 2015 and titled "Methods and Devices for Improving the Functionality of a Powered Human Exoskeleton Device Equipped with a Data Link". The entire content of these applications is incorporated by reference.

FIELD OF THE INVENTION

The present invention relates to devices and methods that augment a wearer's strength and/or aid in the prevention of injury during the performance of certain motions or tasks. More particularly, the present invention relates to devices and methods suitable for therapeutic use with patients that have impaired neuromuscular/muscular function of the appendages or devices suitable for use by people engaging in heavy tool use or weight bearing tasks. These devices each include a set of artificial limbs, with the artificial limbs being movable by actuators under the direction of a control system. The devices potentiate the function of a wearer's appendages for activities including, but not limited to, enabling walking for a disabled person, granting greater strength and endurance in the wearer's arms, or allowing for more weight to be carried by the wearer while walking.

BACKGROUND OF THE INVENTION

Wearable exoskeletons have been designed for medical, commercial, and military applications. Medical exoskeleton devices restore and rehabilitate proper muscle function for patients with disorders affecting muscle control. Medical exoskeleton devices have systems of motorized braces that can apply forces to a wearer's appendages. In a rehabilitation setting, medical exoskeletons are controlled by a physical therapist who uses one of a plurality of possible input means to command an exoskeleton control system. In turn, the exoskeleton control system actuates the position of the motorized braces, resulting in the application of force to, and typically movement of, the body of the wearer. Medical exoskeletons can also be used outside of a therapeutic setting to grant improved mobility to a disabled individual. Commercial and military exoskeletons are used to alleviate loads supported by workers or soldiers during their labor or other activities, thereby preventing injuries and increasing the stamina and strength of these workers or soldiers. Tool-holding exoskeletons are outfitted with tool-holding arms that support the weight of a tool, reducing user fatigue by providing tool-holding assistance. Each tool-holding arm transfers the vertical force required to hold the tool through the legs of the exoskeleton rather than through the wearer's arms and body. Similarly, weight-bearing exoskeletons transfer the weight of an exoskeleton load through the legs of the exoskeleton rather than through the wearer's legs. In some cases, weight-bearing exoskeletons are designed to carry a specific load, such as a heavy backpack. In other cases, military weight-bearing exoskeletons support the weight of armor. Commercial and military exoskeletons can have actuated joints that augment the strength of a wearer, with these actuated joints being controlled by an exoskeleton control system, and the wearer using any of a plurality of possible input means to command the exoskeleton control system.

In powered exoskeletons, exoskeleton control systems prescribe and control trajectories in the joints of the exoskeleton, resulting in movement of the exoskeleton. These trajectories can be prescribed as position-based, force-based, or a combination of both methodologies, such as those seen in impedance controllers. Position-based control systems can be modified directly through modification of the prescribed positions. Similarly, force-based control systems can be modified directly through modification of the prescribed force profiles. Complicated exoskeleton movements, such as walking in an ambulatory medical exoskeleton, are commanded by an exoskeleton control system through the use of a series of exoskeleton trajectories, with increasingly complicated exoskeleton movements requiring an increasingly complicated series of exoskeleton trajectories. These series of trajectories can be cyclic, such as the exoskeleton taking a series of steps with each leg, or they can be discrete, such as an exoskeleton rising from a seated position into a standing position. In the case of an ambulatory exoskeleton, during a rehabilitation session and/or over the course of rehabilitation, it is highly beneficial for the physical therapist to have the ability to modify the prescribed positions and/or the prescribed force profiles depending on the particular physiology or rehabilitation stage of a patient. However, it is complex and difficult to construct an exoskeleton control interface that enables the full range of modification desired by the physical therapist during rehabilitation. In addition, it is important that the control interface not only allow the full range of modification that may be desired by the physical therapist but also that the interface with the physical therapist be intuitive to the physical therapist, who may not be highly technically oriented. As exoskeleton wearers are each differently proportioned, variously adjusted or customized powered exoskeletons will fit each wearer somewhat differently, requiring that the exoskeleton control system take into account these differences in wearer proportion, exoskeleton configuration/customization, and exoskeleton-wearer fit, resulting in changes to prescribed exoskeleton trajectories.

Methods have previously been developed that allow current exoskeletons to transmit exoskeleton diagnostic data to a central server. An example of this type of system is EKSO PULSE™, in which an exoskeleton sends state information, such as time of use or the occurrence of a fall, to a central server. However, the development of a system that allows for the transmission of a range of data from a central server to an exoskeleton control system would also be beneficial. In such a system, the data transmitted to the exoskeleton could be presented to the exoskeleton wearer, used for some function by the exoskeleton control system or both. It would also be useful for the exoskeleton to transmit additional types of data to the central server, allowing for various types of interaction between the exoskeleton control system and the central server. Such a system, in which data is communicated both from an exoskeleton to a central server and from a central server to an exoskeleton, could allow for many applications that would be useful to the exoskeleton wearer, the exoskeleton manufacturer or to third parties.

Based on the above, there exists a need in the art for devices and methods that allow for the transmission of data from a central server to an exoskeleton control system, with the devices and methods also allowing for two-way communication between the exoskeleton control system and the central server in real-time. There also exists a need in the art for devices and methods that allow an exoskeleton wearer to make use of such a communication linkage for applications that increase the usefulness of the exoskeleton to the exoskeleton wearer, including but not limited to applications such as monitoring exoskeleton maintenance needs, monitoring the state of the exoskeleton wearer, receiving alerts, receiving medical or technical support from a virtual or human assistant or navigation of the exoskeleton.

In addition, there exists a need for devices and methods that allow a central server to make use of such a communication linkage for analytic functions that are of value to the central server operator or the exoskeleton wearer, including but not limited to the identification of specific exoskeleton wearers or the use of various data analytics to determine optimal actions for recurring situations and fall mitigation or to determine which therapeutic strategies yield the best outcomes.

Furthermore, there exists a need for devices and methods that allow peripheral devices, including but not limited to crutches, tools, vehicles, replaceable batteries, smartphones, computers or other exoskeletons, to communicate with and be networked to an exoskeleton control system that is in communication with a central server through a data link. There also exists a need for devices and methods that allow an exoskeleton wearer who is not wearing an exoskeleton to communicate with the exoskeleton and/or a central server through use of a peripheral device.

SUMMARY OF THE INVENTION

It is an object of the present invention to provide devices and methods that allow for the transmission of data from a central server to an exoskeleton control system, with the devices and methods also allowing for two-way communication between the exoskeleton control system and the central server in real-time. It is an additional object of the present invention to provide devices and methods that allow for enhancements to and optimization of the two-way transmission of data from the central server to the exoskeleton control system, improving the function, security, and/or efficiency of the two-way data link.

It is a further object of the present invention to provide devices and methods that allow an exoskeleton wearer to make use of such a communication linkage for applications that increase the usefulness of the exoskeleton to the exoskeleton wearer, including but not limited to applications such as monitoring exoskeleton maintenance needs, monitoring the state of the exoskeleton wearer, receiving alerts, receiving medical or technical support from a virtual or human assistant, navigation of the exoskeleton, user interface functions and social or entertainment services. It is also an object of the present invention to provide devices and methods that allow a networked exoskeleton control system and central server to monitor and/or respond to changes in exoskeleton state or exoskeleton wearer state, as well as to record and track state data and response outcomes. In addition, it is an object of the present invention to provide devices and methods that allow a central server to make use of such a communication linkage for analytic functions that are of value to the central server operator or the exoskeleton wearer, including but not limited to the identification of specific exoskeleton wearers or the use of various data analytics to determine optimal actions for recurring situations and fall mitigation or to determine which therapeutic strategies yield the best outcomes.

Furthermore, it is an object of the present invention to provide devices and methods that allow for peripheral devices, including but not limited to crutches, tools, vehicles, replaceable batteries, smartphones, computers or other exoskeletons, to communicate with and be networked to an exoskeleton control system that is in communication with a central server through a data link and for these peripheral devices to be used in various applications that are useful to the exoskeleton wearer. It is also an object of the present invention to provide devices and methods that allow an exoskeleton wearer who is not wearing an exoskeleton to communicate with the exoskeleton and/or a central server through use of a peripheral device.

Concepts were developed for an exoskeleton in which a data link, already existing in some exoskeletons as a way to transmit limited exoskeleton state information back to a central server, is utilized to transmit additional types of data from an exoskeleton control system to the central server, with the central server also utilizing this data link to transmit data to the exoskeleton control system. This two-way transmission of data allows for a variety of useful applications for the exoskeleton wearer, improvements to function of the exoskeleton and new types of central server-based analytics that were previously unavailable. Concepts were further developed for devices and methods that increase the effectiveness and security of the communication between the exoskeleton control system and the central server.

In addition, concepts were developed for ways by which the two-way communication between the exoskeleton control system and the central server could be used for a variety of applications useful to an exoskeleton wearer, including but not limited to applications such as interaction with a virtual or remote physical therapist, interaction with a virtual or remote assistant, user summoned "roadside" assistance, exercise or learning games, social network applications, receiving alerts, user interface settings or features based on exoskeleton wearer skill, user selected system modifications or a custom user- or physical therapist-created data dashboard.

Concepts were also developed for ways by which the two-way communication between the exoskeleton control system and the central server could be used by the central server to analyze data received about the exoskeleton or exoskeleton wearer, including data such as wearer blood pressure or range of motion, exoskeleton performance or maintenance state, power usage in various tasks, wearer performance in a variety of maneuvers or data about the environment that the exoskeleton is operating in. The results of this analysis trigger certain events, including but not limited to summoning of emergency assistance, notification of a physical therapist or technician or lockout or allowance of certain exoskeleton features. Concepts were further developed in which the analysis utilizes machine learning, deep learning, cognitive computing or neuromorphic computing to analyze the data for functions such as predictive failure analysis or optimization of exoskeleton movement or use in various scenarios.

Additionally, concepts were developed for ways by which the communication network between the exoskeleton control system and the central server could be used in order allow the exoskeleton control system to communicate with peripheral devices or other exoskeletons. This allows sharing of data amongst the central server, one or more exoskeletons and a plurality of communication-enabled peripheral devices, with the exoskeleton wearer interacting with this network of systems through the exoskeleton control system and/or one or more peripheral devices. Such peripheral devices include but are not limited to smartphones, smart watches, tablets, Google Glass™-like headsets, personal computers or laptops, crutches, canes, walkers, charging stations, wheelchairs, smart home or office devices (e.g., door locks) and wheelchair-accessible vehicles. Applications for these networked peripheral devices include but are not limited to use of smartphone-based location services, sharing of environmental sensing data by peripheral devices, using sensors to detect the environment (e.g., via Bluetooth™ beacons, Google's Eddystones™ or iBeacons™), networked user interface features, community walking speed detection and gait matching, remote control of exoskeleton devices, exoskeleton sharing services (similar to bike or car sharing services) and exoskeleton swarm walking applications.

In particular, the present invention is directed to systems and methods of communication between a first exoskeleton and a central server or a peripheral device. First data is collected with the first exoskeleton, and the first data is transmitted from the first exoskeleton to the central server or the peripheral device. Second data is generated using the first data, and the second data is transmitted from the central server or the peripheral device to the first exoskeleton or a second exoskeleton.

In one embodiment, an amount of the first data collected with and transmitted from the first exoskeleton varies depending on a movement being performed by the first exoskeleton during collection. The amount of the first data collected with and transmitted from the first exoskeleton can vary depending on a speed or a complexity of the movement being performed by the first exoskeleton. The amount of first data collected with and transmitted from the first exoskeleton can increase when a fall is occurring or likely to occur. The amount of the first data collected with and transmitted from the first exoskeleton is greater when the first exoskeleton is worn by a wearer than when the first exoskeleton is not worn. The amount of the first data collected with and transmitted from the first exoskeleton is greater when the wearer is standing than when the wearer is sitting and greater when the wearer is walking than when the wearer is standing. The amount of the first data collected with and transmitted from the first exoskeleton increases with increased wearer walking speed. The amount of the first data collected with and transmitted from the first exoskeleton is greater when the wearer stands up or sits down than when the wearer is walking.

In another embodiment, the second data is transmitted from the peripheral device to the first exoskeleton, and a movement speed or direction of the first exoskeleton is adjusted based on the second data. The peripheral device can belong to a person other than a wearer of the first exoskeleton. The movement speed or direction of the first exoskeleton is adjusted based on a movement speed or direction of the person. The peripheral device can be another exoskeleton.

In still another embodiment, the second data is transmitted from the peripheral device to the first exoskeleton, and the second data is transmitted from the first exoskeleton to the central server. The second data can be displayed to a wearer of the first exoskeleton. The peripheral device constitutes a first peripheral device, and third data is transmitted from a second peripheral device to a third exoskeleton. The third data is transmitted from the third exoskeleton to the central server, and the second and third data is displayed to a person other than a wearer of the first or third exoskeletons. In a preferred embodiment, the first and second peripheral devices are weapons, the first exoskeleton is worn by a first soldier and the third exoskeleton is worn by a second soldier. The second and third data is displayed to a commander of the first and second soldiers.

In a further embodiment, the first data is collected about a wearer of the first exoskeleton, and movement of the first exoskeleton is modified in real time based on the first data. Additional assistance can be provided to the wearer if the data indicates that the wearer is fatigued. Reduced assistance can be provided to the wearer or movement speed of the first exoskeleton can be increased if the data indicates that a heart rate of the wearer is not sufficiently elevated.

In a still further embodiment, the first data is collected about a wearer of the first exoskeleton, and the first data is transmitted from the first exoskeleton to the central server. Whether the wearer is a known wearer or a new wearer is determined based on the first data. Wearer specific settings are applied to the first exoskeleton if the wearer is a known wearer. The first data can be collected with sensors to create sensor data. The first data can be collected about a gait of the wearer to create gait data. Whether the wearer is a known wearer or a new wearer is determined based on the sensor data or the gait data.

In yet another embodiment, a first copy of an application is run on a control system of the first exoskeleton, and a second copy of the application is run on the central server. In one arrangement, the first exoskeleton is controlled based on the second copy of the application when the first exoskeleton is in communication with the central server, and the first exoskeleton is controlled based on the first copy of the application when the first exoskeleton is not in communication with the central server. In another arrangement, the first exoskeleton is controlled based on the first copy of the application, and the first exoskeleton is controlled based on the second copy of the application if the first copy of the application crashes.

In another embodiment, the first exoskeleton can be caused to enter a restricted mode in which the first exoskeleton is prevented from performing at least some movements, movement speed of the first exoskeleton is limited or movement complexity of the first exoskeleton is limited. The first exoskeleton can be caused to enter the restricted mode based on a level of disability of a wearer of the first exoskeleton, an environment in which the first exoskeleton is being operated or maintenance needs of the first exoskeleton. The first exoskeleton can be caused to enter the restricted mode in response to a fall of the first exoskeleton.

In a further embodiment, the first data is transmitted from the first exoskeleton to the central server. Third data is collected with a third exoskeleton, and the third data is transmitted from the third exoskeleton to the central server. The first data and the third data are analyzed to identify which physical therapy routines or failure responses are most effective or which exoskeleton parts should be redesigned for greater durability.

Additional objects, features and advantages of the invention will become more readily apparent from the following detailed description of the invention when taken in conjunction with the drawings wherein like reference numerals refer to corresponding parts in the several views.

DETAILED DESCRIPTION OF THE PREFERRED EMBODIMENTS

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

Figure 1:
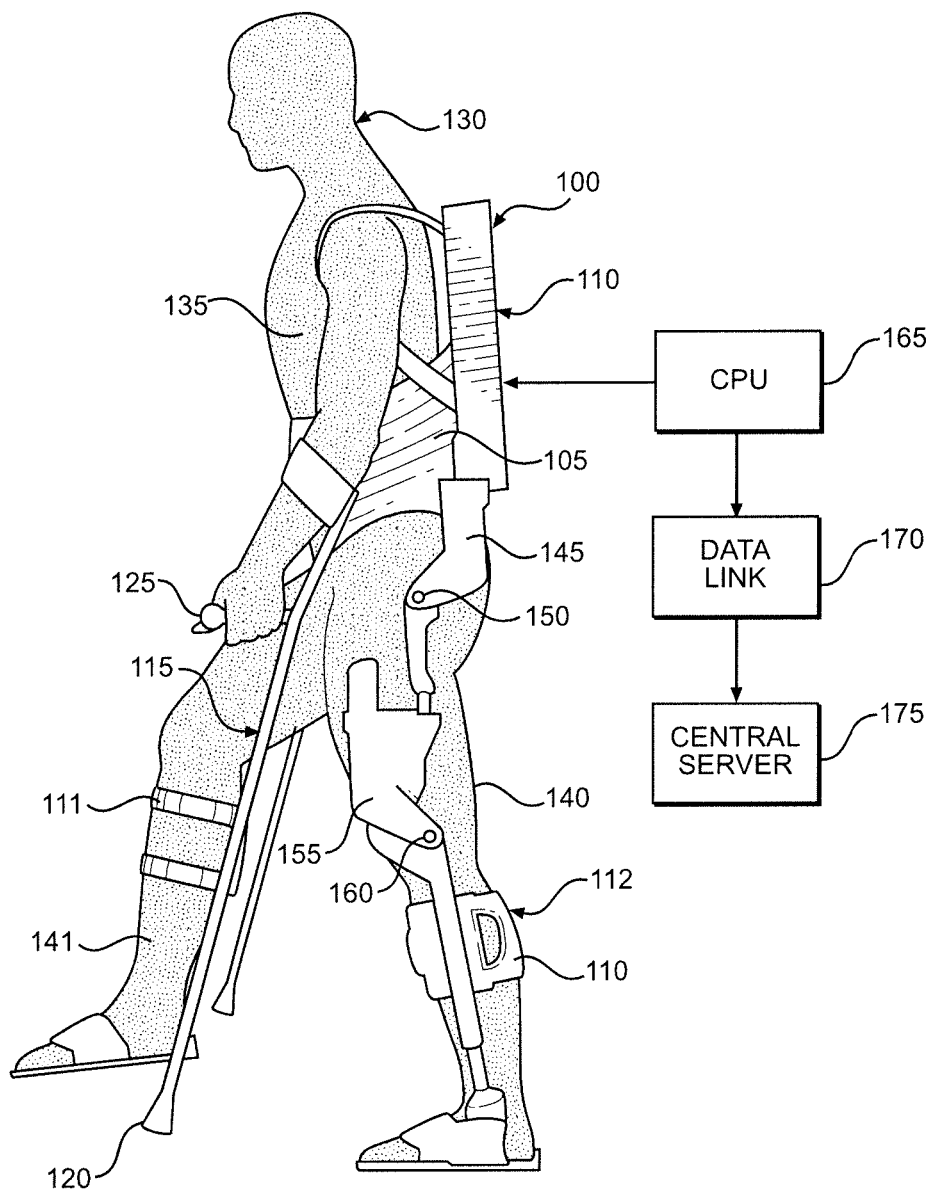
FIG. 1 is a side view of a handicapped individual coupled to an ambulatory exoskeleton, with the control system of the exoskeleton transmitting data to a central server through a data link in accordance with the present invention.

With initial reference to FIG. 1, there is shown an exoskeleton 100 having a torso support 105 and lower leg supports 110 and 111. Exoskeleton 100 is used in combination with a pair of crutches, a left crutch 115 of which includes a lower, ground-engaging tip 120 and a handle 125. In connection with this embodiment, through the use of exoskeleton 100, a patient (or, more generally, a user or wearer) 130 is able to walk. In a manner known in the art, torso support 105 is configured to be coupled to a torso 135 of patient 130, while leg supports 110 and 111 are configured to be coupled to lower limbs 140 and 141 of patient 130. Additionally, actuators are interposed between portions of leg supports 110 and 111 as well as between leg supports 110 and 111 and torso support 105, with these actuators being configured to shift leg supports 110 and 111 relative to torso support 105 to enable movement of lower limbs 140 and 141 of patient 130. In some embodiments, torso support 105 can be quite small and comprise a pelvic link (not shown), which wraps around the pelvis of patient 130. In the example shown in FIG. 1, the actuators are specifically shown as a hip actuator 145, which is used to move a hip joint 150 in flexion and extension, and as a knee actuator 155, which is used to move a knee joint 160 in flexion and extension. Actuators 145 and 155 are controlled by a controller (or control system or CPU) 165 in a plurality of ways known to one skilled in the art of exoskeleton control. Although not shown in FIG. 1, various sensors are in communication with controller 165 so that controller 165 can monitor the orientation of exoskeleton 100. Such sensors can include, without restriction, encoders, potentiometers, accelerometer and gyroscopes, for example. In addition, controller 165 is in either continuous or intermittent communication with, and transfers selected exoskeleton state data to, a data link 170. Data link 170 is a wireless transmission device that is configured to transfer data received from controller 165 to a central server 175. As the particular structure of an exoskeleton for use in connection with the present invention can take various forms known in the art, it will not be detailed further herein.

Figure 2A:
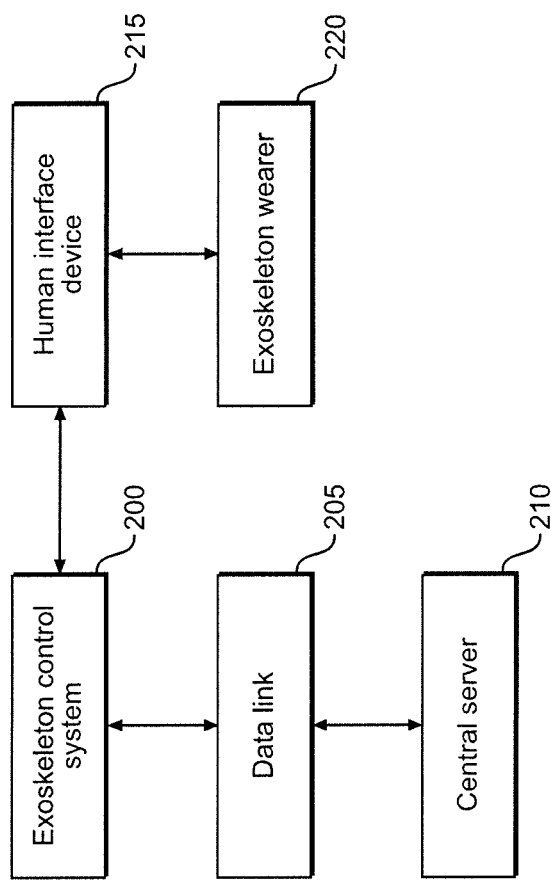
FIG. 2A is a block diagram of the parties communicating in a first embodiment of the present invention.
Figure 2B:
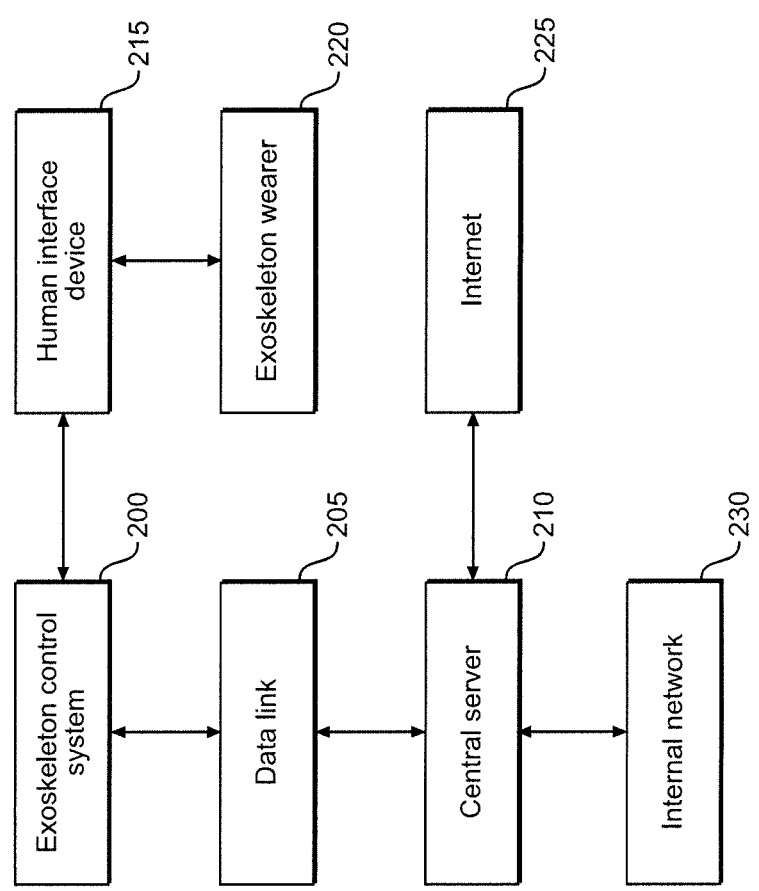
FIG. 2B is a block diagram of the parties communicating in a variation of the first embodiment.

Turning to FIGS. 2A and 2B, block diagrams of the parties in communication in the first embodiment of the present invention are shown. Specifically, in FIG. 2A, an exoskeleton control system 200 is in communication with a data link 205, which is in communication with a central server 210. Through data link 205, control system 200 is able to send data to and receive data from central server 210. Control system 200 is also in communication with a human interface device 215, which interacts with an exoskeleton wearer 220. As a result, wearer 220 can interact with control system 200. Since control system 200 is in communication with central server 210, wearer 220 can also interact, indirectly, with central server 210. In FIG. 2B, a variation of the first embodiment is shown in which central server 210 is additionally in communication with the Internet 225 and/or an internal network 230. This allows interaction between wearer 220 and data or entities on the Internet 225 or a specific internal network, i.e., internal network 230. In some embodiments, data link 205 is a wireless device that transmits and receives data in any of a plurality of ways known in the art. In some embodiments, the exoskeleton has multiple data links that are in communication with control system 200 and central server 210, with differing data links being used for different types of data or levels of communication security. For example, the exoskeleton can have one encrypted data link and one unencrypted data link. In some embodiments, the exoskeleton frame is utilized as an antenna array for wireless amplification and omnidirectional coverage. In some embodiments, human interface device 215 is a simple control panel with a small screen and speaker. In other embodiments, human interface device 215 makes use of more complicated input systems, such as voice or gesture recognition, and provides haptic wearer feedback. However, it should be recognized that a variety of input and feedback mechanisms known in the art can be used in connection with the present invention, with these mechanisms making use of systems already present in the exoskeleton or additional components. In some embodiments, additional sensors present in the exoskeleton, such as GPS or other geo-positioning devices, video cameras or other sensors known in the art, are used to transmit useful data to control system 200 and central server 210.

As an example of the first embodiment of the present invention, consider a patient using an ambulatory exoskeleton for long term rehabilitative therapy as well as for personal mobility. By making use of the first embodiment, the patient can use his or her exoskeleton for physical mobility activities, with exoskeleton state data being reported to a central server. This allows the central server to either perform some analysis on the use of the exoskeleton by the patient or transfer the data to a third party, such as a physical therapist, who can also perform some analysis on the use of the exoskeleton by the patient. The first embodiment also allows the central server to relay data back to the exoskeleton so that the patient receives feedback from the central server, or the physical therapist, as to their use of the exoskeleton. It is also possible for the patient, though the communication apparatus of the first embodiment, to communicate in real time with a person connected to the central server, e.g., the physical therapist. In addition, the first embodiment provides for more mundane types of communication between the patient and various parties connected to the central server, such as billing transactions based on exoskeleton use, the results of a particular physical therapy session, scheduling additional physical therapy sessions and technical "help-desk" functions in which the patient can ask questions regarding the operation of the exoskeleton. If, as in some embodiments, the central server is connected to the Internet, the first embodiment can allow the patient to access email or other web-based services through an exoskeleton-wearer interface, i.e., a human interface device. In a further example of the first embodiment, the exoskeleton can monitor other electronic medical records and alert the physical therapist to adaptations to the therapy that should be made to account for other treatments the patient is receiving.

Collection and transmission of data from an exoskeleton control system to a central server is important for monitoring the health of the exoskeleton system, as well as for many other possible applications of the first embodiment of this invention. However, in general, it is difficult to return all data from the exoskeleton at the highest sampling rates because the volume of data generated is tremendous and the data is transmitted wirelessly to the central server. In addition, some, or even much, of the available data collected by the exoskeleton control system during certain exoskeleton activities, or lack of activity, is not useful enough to merit transmission. Thus, attempting to transmit all data from an exoskeleton control system over a wireless system will likely result in exorbitant costs and/or potentially large gaps in the data because the wireless data collection will not be able to keep up with the data generation rate. In connection with a second embodiment of the present invention, a solution to this problem was developed that is rooted in the nature of exoskeleton devices such as mobile walking systems—the amount of data collected or transmitted can be throttled or expanded based on the activity of the exoskeleton. In general, the most interesting data occurs when the motion of the machine is fastest or most dynamic—there is the greatest chance of error and the frequencies in data reported by the sensors will be the highest. In a particularly dynamic motion the sensors could even be "oversampled" beyond the control frequency of the exoskeleton so that faster dynamics can be captured.

Figure 3A:
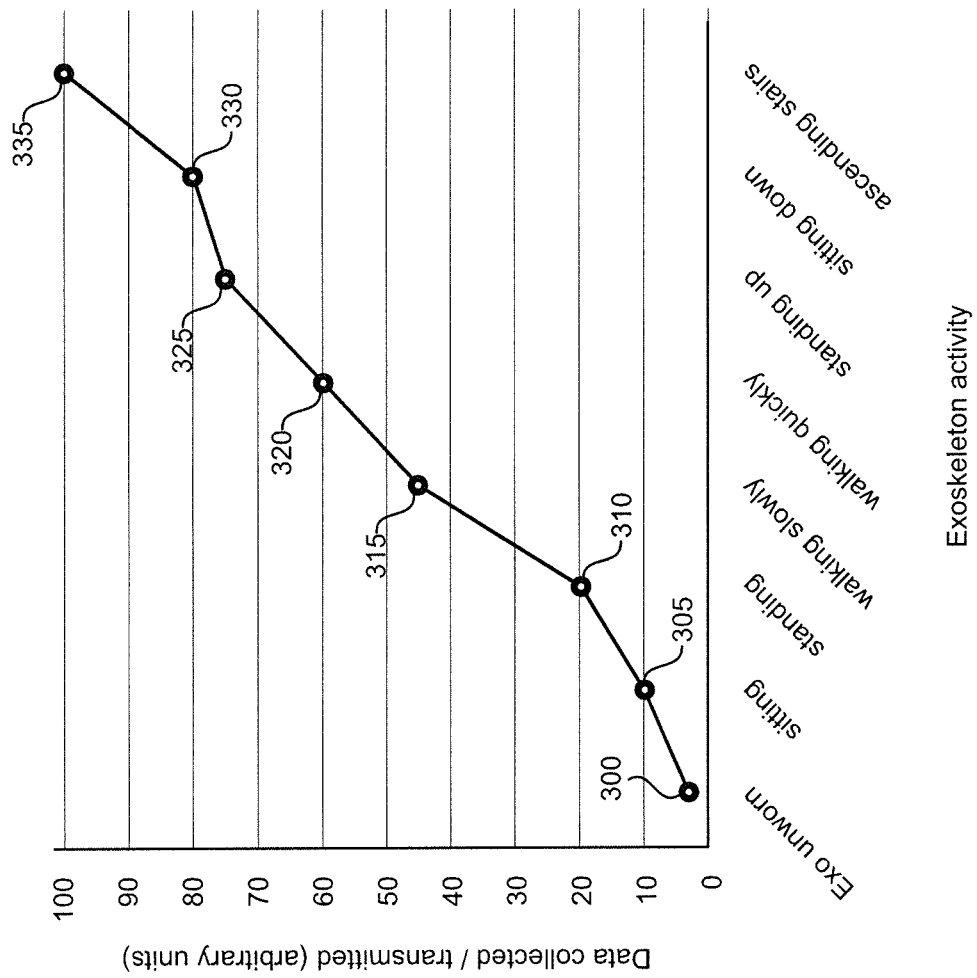
FIG. 3A is a graph illustrating variable data collection/transmission in accordance with a second embodiment of the present invention.

To illustrate the second embodiment of the present invention, which improves on the function of the two-way data link of the first embodiment, a graph is shown in FIG. 3A. In the graph, the y-axis shows the data quantity, in arbitrary units, collected by the exoskeleton and transmitted to the central server though the data link, while the x-axis shows the exoskeleton activity type. A plot represents the data collection/transmission rate for each exoskeleton activity. In this representation, very little data is collected/transmitted when the exoskeleton is not being worn (as shown at 300), whereas more data is collected/transmitted when the exoskeleton is worn by a person in a sitting position (as shown at 305). Increasingly large amounts of data are collected and transmitted as the exoskeleton is used for increasingly complicated activities, such as standing (310), walking slowly (315), walking quickly (320), standing up from a seated position (325) and sitting down from a standing position (330), ultimately reaching the highest rate of data collection/transmission when the exoskeleton is performing a very complicated activity, which is shown in FIG. 3A as ascending stairs (335). In this embodiment, it is generally not necessary to return the full rate of data unless the motion of the machine is particularly fast. For example, if the exoskeleton is falling or in a situation in which a fall is more likely, it can be advantageous to oversample the inertial sensors (e.g., accelerometers and rate gyros) so that more information about the impact is available to ascertain whether the wearer or exoskeleton was damaged during the impact. In some embodiments, in such a situation, additional data from peripherals that is not normally returned can also be collected. In some embodiments, after data is collected at a high sampling rate in a high-risk maneuver, if no fall is subsequently detected, the data can be down sampled retrospectively after the event in order to save space during the uploading process. Similarly, in some embodiments, certain types of data can be stored for a short period of time in a buffer, and this stored data can be later transmitted or not depending on the satisfaction of certain conditions. At the other extreme, when the exoskeleton is on but not worn and is not moving, the data rate can be at its lowest point, or possibly even zero, since no errors are expected to be encountered and there is no dynamic motion. In some embodiments, less data can be transmitted from the exoskeleton to the central server in order to allow more data to be received from the server or vice versa.

As an example of the second embodiment of the present invention, consider a physical therapy clinic that uses exoskeletons for ambulatory therapy. This clinic will want to collect data on exoskeleton performance under certain conditions for various patients in a range of rehabilitative states, with the data relating to failure events, such as slips or falls, and advanced movements being of value to designing improved physical therapy sessions. However, the collection of massive volumes of data would overwhelm both the ability to store data as well as the ability to quickly and/or effectively analyze the collected data. By making use of the second embodiment, more data will be collected relating to the most interesting exoskeleton-related events and movements, and little or no data will be collected from the exoskeletons when the exoskeletons are in a resting state, thereby allowing a more manageable amount of data to be collected, stored and analyzed.

Figure 3B:
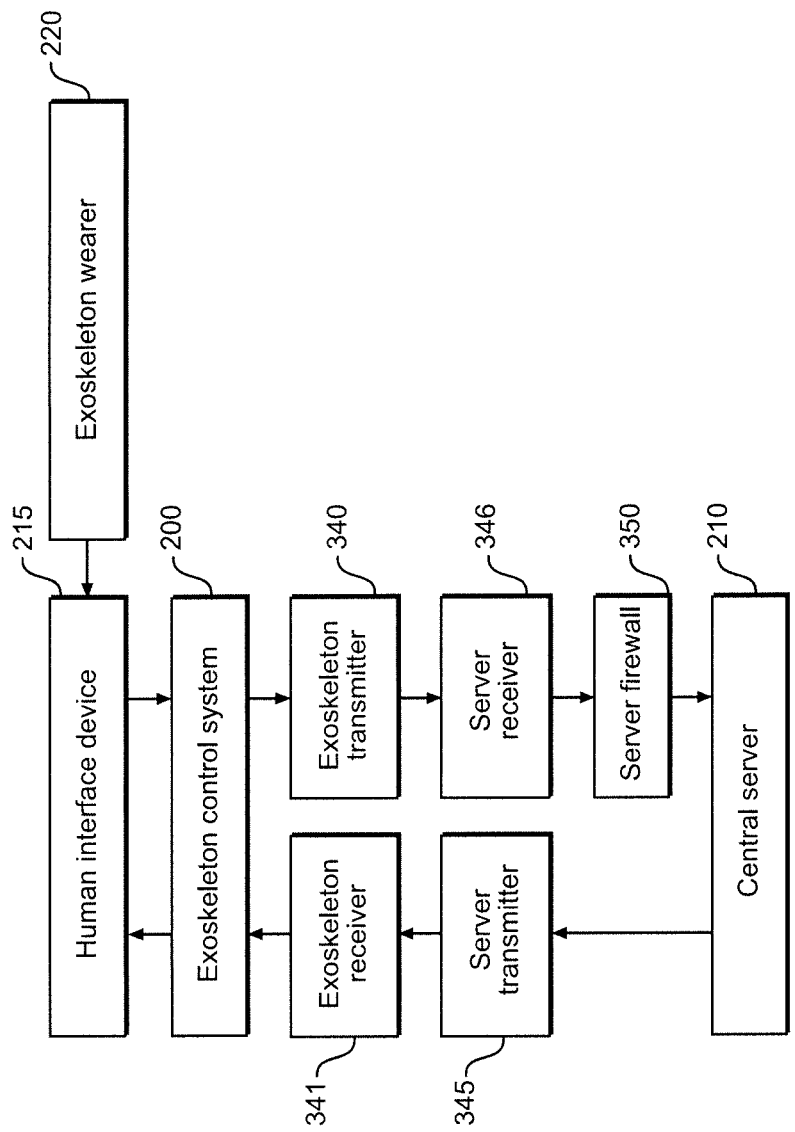
FIG. 3B is a block diagram of the parties communicating in the second embodiment.

With reference to FIG. 3B, another aspect of the second embodiment, which improves on the function of the two-way data-link of the first embodiment, is shown as a block diagram. Again, control system 200 is in communication with human interface device 215, which interacts with wearer 220. Control system 200 is additionally in communication with two separate exoskeleton data links. Specifically, control system 200 sends data to an exoskeleton transmitter 340 and receives data from an exoskeleton receiver 341. Exoskeleton receiver 341 receives wireless signals from a server transmitter 345, and exoskeleton transmitter 340 transmits wireless signals to a server receiver 346. Central server 210 sends data to server transmitter 345 and receives data from server receiver 346, with the data from server receiver 346 first being controlled and/or filtered by a server firewall 350. In this way, the data sent from central server 210 to control system 200 follows a different path than the data sent from control system 200 to central server 210. This allows data bandwidth usage from a send function to not interfere with data bandwidth usage from a receive function. Also, differential levels of security can be utilized for each path. For example, in FIG. 3B, greater security is provided for central server 210 through the use of server firewall 350. In some embodiments, more than two data transmission paths exist. In some embodiments, the exoskeleton also has a firewall controlling all data passed from exoskeleton receiver 341 to control system 200.

As an example of this aspect of the second embodiment of the present invention, in which multiple communication devices and pathways make up the two-way data link between the exoskeleton control system and the central server, consider an exoskeleton wearer that in engaged in an application requiring both transmission and reception of large volumes of data. For instance, if the wearer were engaging in a two-way video chat with a physical therapist, the physical therapist might be receiving large volumes of data relating to the exoskeleton state, including data on exoskeleton trajectories, video data and voice or other communication from the wearer. Simultaneously, the wearer is receiving real-time feedback and direction from the physical therapist. By incorporation of this aspect of the second embodiment into the data link, two high-bandwidth communication pathways, one from the exoskeleton to the central server and one from the central server to the exoskeleton, can exist at the same time without interfering with and diminishing the rate or quality of one another.

Upon the establishment of a functional two-way data link between an exoskeleton control system and a central server, as provided for in the first embodiment and improved upon in the second embodiment, a number of more advanced applications are made possible, with these applications being additional embodiments of the present invention.

The third embodiment of the present invention provides solutions to several issues relating to the linked activities of exoskeleton navigation and exoskeleton power monitoring in an unstructured (i.e., non-clinic) environment. It is undesirable for an exoskeleton and wearer to be out of the house or clinic and run out of battery power in a location where the wearer is unable to recharge the exoskeleton. The third embodiment is an advanced power monitoring scheme, with both an exoskeleton control system and a central server communicating in such a way as to predict power usage under specific conditions and navigational options. In this scheme, the exoskeleton control system monitors exoskeleton power given the type of action the wearer is engaged in at the time, the wearer's weight, the wearer's spasticity and residual strength, the wearer's fatigue levels and the exoskeleton location's from integral exoskeleton GPS systems. The exoskeleton control system then communicates this data to the central server. The central server uses the data provided by the exoskeleton control system in tandem with terrain and metrics data to predict how much power is needed per step or per action, allowing predictions of battery discharge rate, remaining range and time to possible destinations. The estimated range of the exoskeleton can be reported to the user, via a human interface device such as a control pad or any of a number of feedback means known in the art. Furthermore, the user can input a goal location or activity, and the exoskeleton control system and central server can determine if there is sufficient charge for that activity. In some embodiments, this system includes features assuring that there is enough power for a round trip of exoskeleton travel and warning the exoskeleton wearer if there is a risk of insufficient power for a selected task or trip. In some embodiments, the communication link between the exoskeleton control system and the central server can also be used by the wearer to locate the nearest services, such as battery charging or medical services, or the locations of other exoskeleton wearers that might be able to provide assistance. In some embodiments, devices are added to the exoskeleton to allow the exoskeleton to make use of specific available types of battery charging interfaces, such as automobile battery charging stations. In some embodiments, battery charging devices allow the exoskeleton battery to be charged using other less optimal power sources, such as vehicular power or domestic wall outlets, with the central server also directing the wearer to these other power sources. In some embodiments, the exoskeleton is configured to use swappable, pre-charged battery packs that can be made available in certain locations known to the exoskeleton navigation system. In such an embodiment, it is preferable that the exoskeleton be configured to use both a primary battery and a secondary battery so that exoskeleton power can be maintained while one battery is being changed. In some embodiments, the navigational interface can be used by the exoskeleton wearer to interface with social networking or similar applications, allowing the wearer to be provided with information such as disability accommodation, special entrances, seating limitations or other information that would be useful to the wearer in selecting a destination or path.

Figure 4:
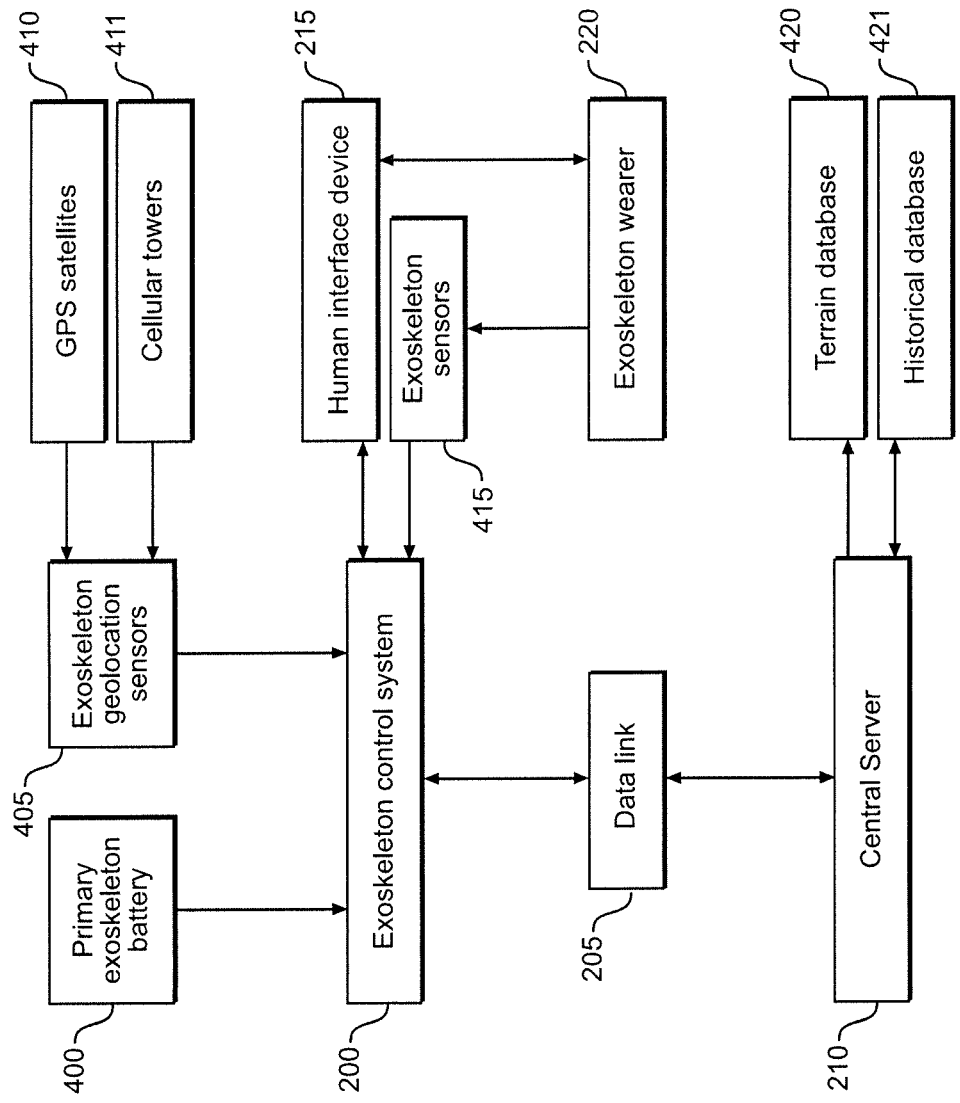
FIG. 4 is a block diagram of the parties communicating in a third embodiment of the present invention.

Turning to FIG. 4, a block diagram representing the third embodiment of the present invention is shown. Control system 200 continuously receives data on remaining power from a primary exoskeleton battery 400 as well as location data from exoskeleton geolocation sensors 405. Geolocation sensors 405 receive location related data from GPS satellites 410 and/or cellular towers 411. Control system 200 also continuously receives data relating to exoskeleton use and the state of wearer 220 from exoskeleton sensors 415. Control system 200 then sends the accumulated data to central server 210 through data link 205. Central server 210 makes use of the data from control system 200 as well as information from a terrain database 420 and a historical database 421. Historical database 421 contains accumulated data regarding previously reported power usage and navigational data from a large sampling of exoskeletons and wearers as well as specific historical data relating to wearer 220. Using all of this data, central server 210 is able to estimate the discharge rate of primary exoskeleton battery 400 for a given activity or navigational option, with this estimate being sent to control system 200 through data link 205, at which point the estimate can be displayed to wearer 220 via human interface device 215. Wearer 220 can then input commands or queries into human interface device 215, with these commands or queries being sent to central server 210 by way of control system 200 and data link 205. At this point, central server 210 can adjust estimates or propose alternative actions, which are then relayed back to wearer 220 by way of data link 205, control system 200 and human interface device 215.

As an example of the third embodiment of the present invention, consider a disabled individual who is using an ambulatory exoskeleton for mobility purposes and who wishes to visit a specific location. By making use of the third embodiment, an exoskeleton control system and central server can report to the individual whether he or she has enough power to walk to the location and also whether he or she is predicted to have enough power to return. If the system predicts that there is insufficient remaining power to return, the system can report to the individual the locations along the pathway that can be used to recharge the exoskeleton and thereby make the walk possible.

It is generally desirable to determine when an exoskeleton will need service so that service can occur before a failure. While such maintenance services are common to all expensive equipment, exoskeletons undergo a particularly broad range of forces and loads that can damage components, and failures in exoskeleton components can put an exoskeleton wearer at risk of injury. One further complication is that disabled exoskeleton wearers might not have sensation in certain portions of their bodies, requiring additional care to be taken to assure proper operation of exoskeleton components. The fourth embodiment of the present invention addresses the risk of exoskeleton component failure through the use of predictive maintenance, which is done by monitoring the loadings at specific components on each exoskeleton and communicating this information to a central server. The central server then compares these loadings to failure rates in other test exoskeletons and deployed exoskeletons, allowing the central server to better predict failures in exoskeletons in the field. This type of monitoring also has an important regulatory component in assuring regulators, such as the Food and Drug Administration, that an exoskeleton is safe across a range of users. By using a large enough database of device failures, it can be shown that an exoskeleton device is safe even under aggressive use, providing important risk mitigation during design. This would allow exoskeletons to be tested in certain situations or use cases by able-bodied users prior to exoskeleton use in these situations by disabled individuals. In some embodiments, the exoskeleton can be programmed to disallow further use (or specific types of use) until required maintenance is completed. In some embodiments, only certain types of maintenance will disable the exoskeleton, or only certain maneuvers will be disabled until maintenance is performed. In some embodiments, when an error is triggered by the exoskeleton, an automatic report is generated and communicated back to the central server for analysis. Also, a further evaluation of the need for maintenance or further inspection of the exoskeleton is triggered. In some embodiments, the system of the fourth embodiment is used to determine which exoskeleton parts should be redesigned for greater durability. In some embodiments, in the event of certain actual or predicted exoskeleton equipment problems, the system prompts a call for assistance, similar to that used by roadside assistance for automobiles, and can utilize a GPS location device coupled to the exoskeleton or some other two-way communication system, as described above.

Figure 5:
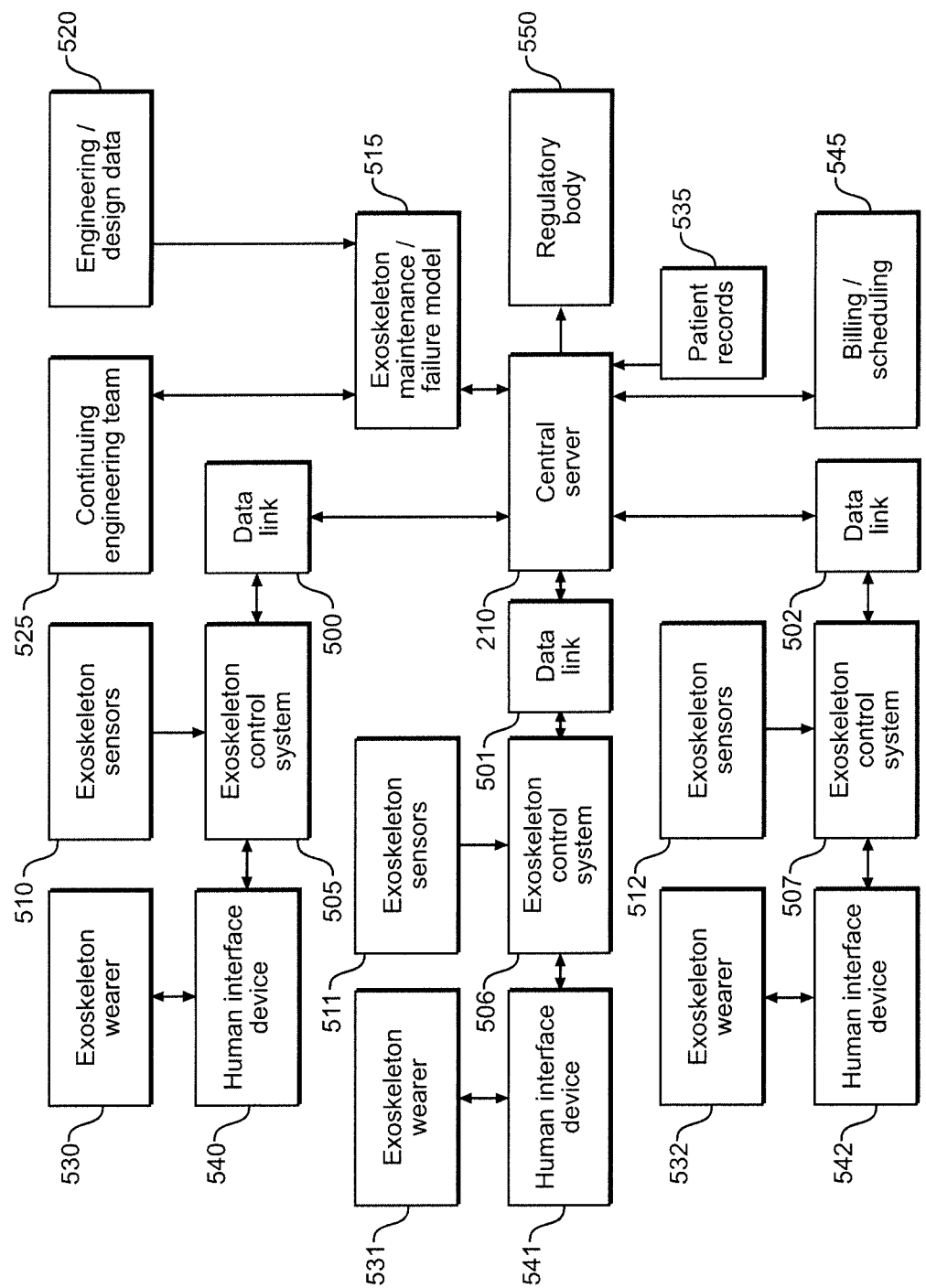
FIG. 5 is a block diagram of the parties communicating in a fourth embodiment of the present invention.

With reference to FIG. 5, there is shown a box diagram representing the fourth embodiment of the present invention. In this embodiment, three exoskeletons are communicating data to central server 210, which builds a failure model using the aggregate communicated data, design data, engineering team input and patient records. A required maintenance schedule is returned to each exoskeleton, and aggregate data is provided to the engineering team for diagnostics and to a regulatory body to show safety. Central server 210 is in communication with the exoskeletons through data links 500, 501 and 502, which relay exoskeleton state data from exoskeleton control systems 505, 506 and 507. Control systems 505-507 receive exoskeleton state and function data from exoskeleton sensors 510, 511 and 512, allowing central server 210 to monitor the state and function of each exoskeleton. Central server 210 uses the data received from the exoskeletons not only to monitor the current state of those exoskeletons, but also to build, over time and using many exoskeletons, an exoskeleton maintenance and failure model 515. Model 515 also takes into account engineering and design data 520 and input from a continuing engineering team 525. Central server 210 then analyzes the data from a single exoskeleton, e.g., the exoskeleton controlled by control system 505, worn by an exoskeleton wearer 530 and transmitting data from exoskeleton sensors 510 via data link 500. Central server 210 also analyzes patient records 535 for wearer 530 and applies the data from exoskeleton sensors 510 and patient records 535 to model 515 to determine the need for exoskeleton maintenance. If central server 210 determines that the exoskeleton is in need of maintenance, central server 210 sends a message by way of data link 500 and control system 505 to a human interface device 540 in order to inform wearer 530 of the need for maintenance. Central server 210 then coordinates with wearer 530 and a billing and scheduling department 545 to arrange exoskeleton maintenance. In addition, central server 210 reports data, as well as model 515, to a regulatory body 550 in order to demonstrate the ongoing safety of the exoskeleton system.

As an example of the fourth embodiment of the present invention, consider a situation in which there are two ambulatory exoskeletons, each exoskeleton being the same model and age but belonging to a different wearer. One exoskeleton is worn by a light wearer and is used on a smooth floor indoors without ever falling, thereby requiring less frequent maintenance relative to the other exoskeleton, which is worn by a heavy wearer on concrete outside who falls occasionally due to aggressive exoskeleton use. Based on data transmitted to a central server from each exoskeleton control system, the history of machine failures, information about the exoskeleton design and an analysis of engineering staff, it is possible for the central server to forecast a schedule of maintenance that is then communicated back to the exoskeletons in the field. Thus, the light user will not need to go in for unnecessary maintenance and the heavy user will go in more often than normal but will not need to be concerned about a machine failure despite his or her aggressive exoskeleton use.

An ambulatory exoskeleton can, based on configuration and sensors present, provide a substantial amount of information about a wearer's performance and state, thereby serving as an ideal basis for monitoring the entire body system of the wearer. The fifth embodiment of the present invention provides ways by which an exoskeleton control system can serve as a basis for a local network or "body area network" for a variety of sensors to respond or report to. In this way, data can be synced on the same clock and compared. This exoskeleton "body area network" is additionally in communication with a central server in order to allow remote monitoring or analytic functions. Sensors that can be used to gain further information about the exoskeleton wearer include but are not limited to electroencephalography (EEG), electromyography (EMG), electrocardiography (EKG), pulse, blood pressure and body temperature sensors. Exoskeletons can also be used to identify specific users based on gait biometrics or other unique markers, with the exoskeleton connection to the central server through the two-way data link allowing for identification of users who are new to a particular exoskeleton. As a result, centralized settings for exoskeletons and users can be automatically applied. In addition, an exoskeleton with a "body area network" can be used to remotely monitor the health of an exoskeleton wearer, allowing for summoning of emergency or other services in certain cases. For exoskeleton wearers with a disability resulting in loss of sensation in some part of the body, the "body area network" can be used for early detection of pressure sores directly or due to changes in gait. In a therapeutic setting, a "body area network" in combination with communication with a central server can be used for automatic range of motion tests with remote monitoring, monitoring and adjusting the course of physical therapy or effecting the application of anti-inflammatory, analgesic or other medication in response to sensor data.

Figure 6:
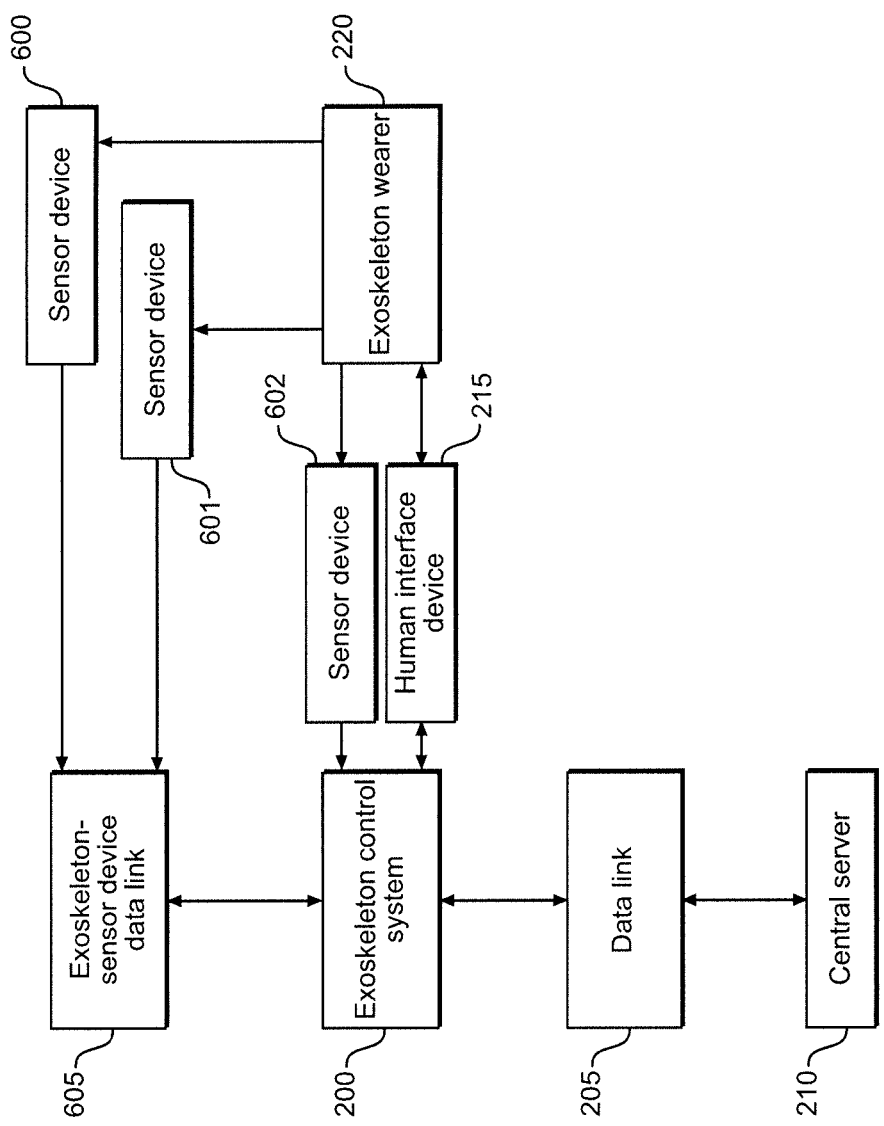
FIG. 6 is a block diagram of the parties communicating in a fifth embodiment of the present invention.

FIG. 6 shows a block diagram representing the fifth embodiment of the present invention. Exoskeleton wearer 220 is monitored by sensor devices 600, 601 and 602. Sensor device 602 is wired directly to and transfers data to exoskeleton control system 200, while sensor devices 600 and 601 are in wireless communication with an exoskeleton-sensor data link 605 that transfers sensor data to control system 200. In this way, control system 200 collects a variety of data about wearer 220. Control system 200 is also in communication with central server 210 through data link 205, which can be considered an exoskeleton-server data link. This allows the state of wearer 220 to be monitored and/or analyzed by both control system 200 and central server 210, with the results of this analysis being, in some cases, made available to wearer 220 though human interface device 215.

As an example of the fifth embodiment of the present invention, consider a patient wearing an exoskeleton equipped with a "body area network" during a physical therapy session. A heart rate monitor can be attached that communicates with the exoskeleton in a manner similar to a heart rate monitor communicating with a treadmill. However, because the exoskeleton is providing both the control and motion, these sensors can either be passive in that the information is simply reported or they can be used in the exoskeleton control system. For example, EMG sensors can be used to monitor muscle fatigue. As the muscles fatigue, the exoskeleton controller can respond by providing additional power. The sensors can also provide input to allow the exoskeleton to challenge the wearer. For example, if the wearer's heart rate is not elevated, the exoskeleton can speed up or require more input from the wearer. Sensors can also report to the "body area network" when the exoskeleton is not in use. For example, a GPS watch, health/activity monitoring watch or sleep monitoring device can report back to the exoskeleton, thus providing more information as to the overall well-being of the exoskeleton wearer. This information can be used by the exoskeleton control system or the networked central server in order to modify the course of therapy or to signal a medical professional to further evaluate the data on the patient's health. In another example, collected health data such as step counts and caloric expenditure can be automatically uploaded to social networks with the intent of sharing progress or gamifying rehabilitation by setting competitive goals.

Figure 7:
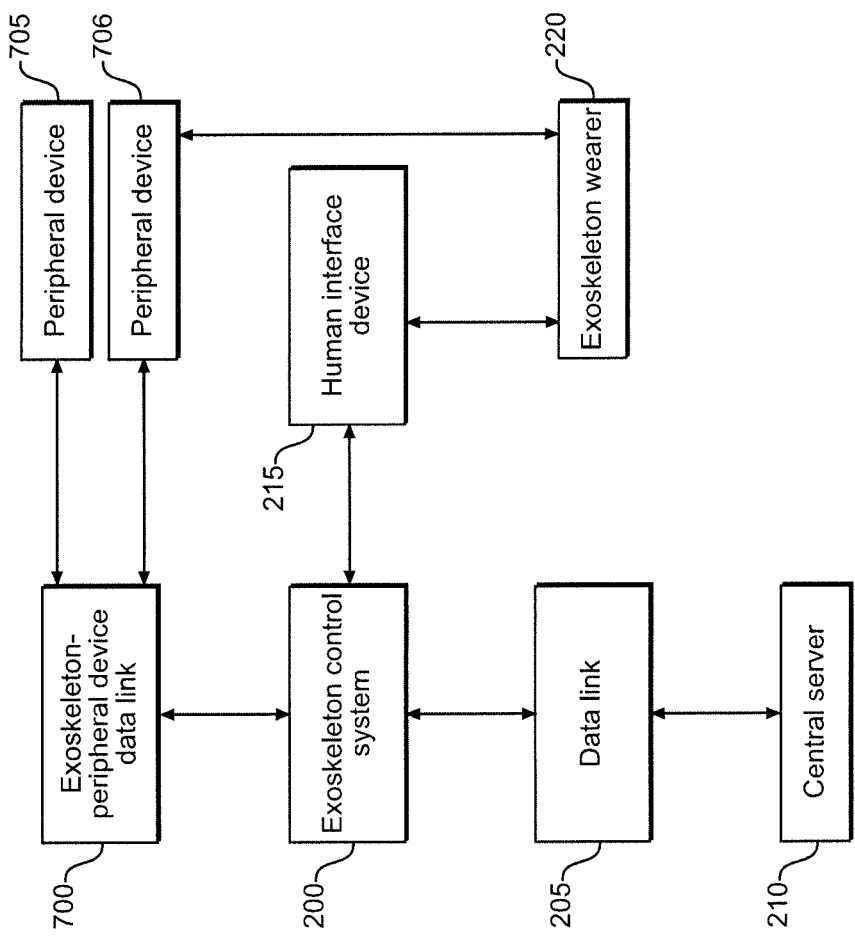
FIG. 7 is a block diagram of the parties communicating in a sixth embodiment of the present invention.

Previously described embodiments of the present invention have allowed an exoskeleton control system to be networked to a central server or physiological sensors in a "body area network". The sixth embodiment of the present invention makes use of similar communication devices and methods, allowing the exoskeleton control system to be networked with additional peripheral devices. These peripheral devices can include devices such as: crutches equipped with sensors or input/feedback interfaces; specific human interface devices such as Google Glass or other hands-free interfaces; automobiles; wheelchairs; smartphones; tablets; smart watches; entertainment consoles; swappable battery packs; environmental sensing devices; medical devices such as glucose sensors; tools; other exoskeletons; or even simple RFID devices embedded in walls, appliances or other features to improve navigation in confined spaces. FIG. 7 is a block diagram representing the sixth embodiment and shows exoskeleton control system 200 in communication with an exoskeleton-peripheral device data link 700, which is in communication with peripheral devices 705 and 706. Peripheral device 706, which is a device such as a crutch, is also in direct interaction with exoskeleton wearer 220. Wearer 220 is able to interact with control system 200 through human interface device 215, which allows wearer 220 to interact with peripheral devices 705 and 706 using human interface device 215. Control system 200 is also in communication with central server 210 though data link 205, which can be considered an exoskeleton-server data link. This allows central server 210 networked access to data from peripheral devices 705 and 706.

As an example of the sixth embodiment of the present invention, consider a soldier on the battlefield wearing a military exoskeleton. By making use of the sixth embodiment, the soldier can network peripheral devices to an exoskeleton control system. For example, the firearm of the soldier can communicate the quantity of ammunition remaining in the soldier's magazine to the exoskeleton control system, with this quantity then being relayed to the soldier through a heads-up-display peripheral device that is also networked to the exoskeleton control system. Information on remaining ammunition, frequency of ammunition use or targeting information can be relayed from the exoskeleton control system to a central server, where battlefield commanders can monitor the actions and remaining resources of a unit. Orders can then be relayed from the central server to the exoskeleton control system, at which point the orders are relayed to the soldier through a human interface device.

In a seventh embodiment of the present invention, a central server performs data analytics tasks using data provided by the control systems of a deployed fleet of exoskeletons. This data includes linked and unlinked datasets on exoskeleton location and movement, power usage in various tasks, wearer performance in a variety of maneuvers, body sensor data and/or peripheral device data. These datasets provide a wealth of information that can be sorted and analyzed using techniques known in the art of big data analytics and deep learning. This analysis facilitates improvements to exoskeleton design, physical therapy routines, responses to failures, navigation from point-to-point and a host of other functions of use to exoskeleton designers or wearers.

As an example of the seventh embodiment of the present invention, consider a central server that is in communication with hundreds of exoskeletons that are being used in clinical therapy settings. The data accumulated from the control systems of these exoskeletons and relayed to the central server via data links can be used to determine optimal points to recharge or discharge batteries in order to provide for maximum battery life. Then, new instructions are relayed from the central server to the control systems, and optionally through human interface devices to the exoskeleton wearers, relating to determined best use parameters for the exoskeletons in terms of maximizing battery life.

Figure 8A:
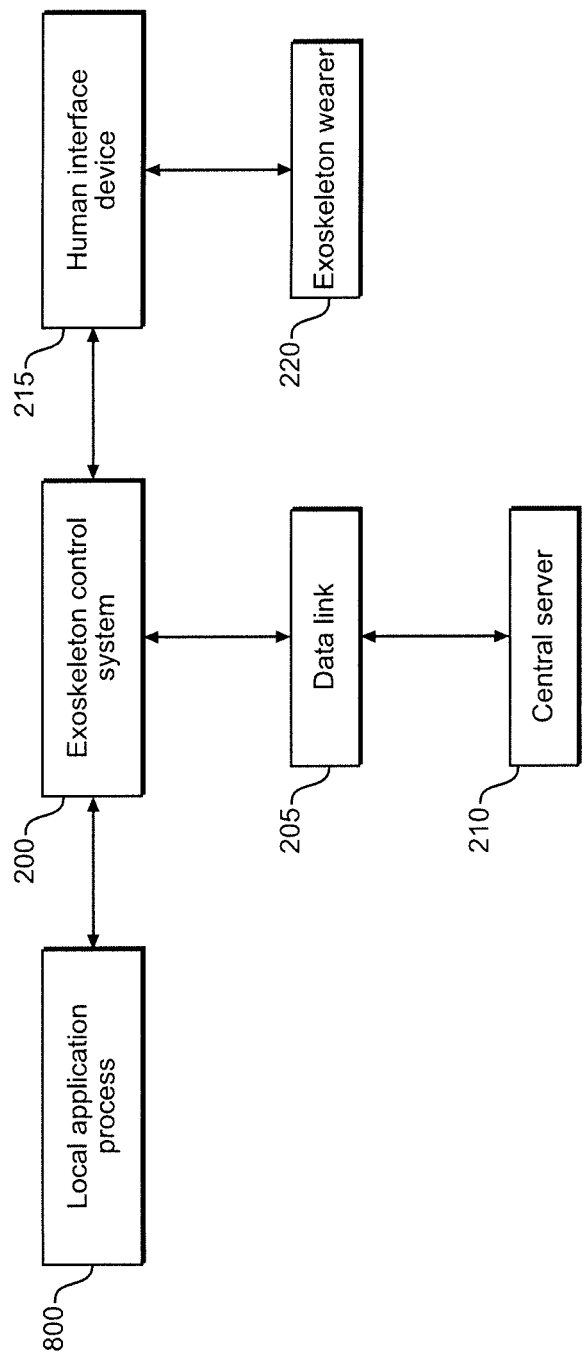
FIG. 8A is a block diagram of the parties communicating in an eighth embodiment of the present invention.

With reference now to FIG. 8A, a block diagram shows the parties in communication in an eight embodiment of the present invention. As discussed above in connection with the first embodiment, exoskeleton control system 200 is in communication with data link 205, which is in communication with central server 210. Through data link 205, control system 200 is able to send data to and receive data from central server 210. Control system 200 is also in communication with human interface device 215, which interacts with exoskeleton wearer 220. As a result, wearer 220 can interact with control system 200. Since control system 200 is in communication with central server 210, wearer 220 can also interact, indirectly, with central server 210. A local application process 800 runs on control system 200. Wearer 220 is able to interact with local application process 800 through human interface device 215, and central server 210 is able to interact with local application process 800 though data link 205, thereby allowing local application process 800 to transmit information to and from both central server 210 and wearer 220. In some embodiments, the communication between control system 200 and central server 210 is constant. In other embodiments, the communication between control system 200 and central server 210 is intermittent. Since local application process 800 is located on control system 200, communication to central server 210 can be disrupted without preventing wearer 220 from accessing local application process 800.

As an example of the eighth embodiment of the present invention, consider a disabled person using an ambulatory exoskeleton for both therapeutic and mobility purposes. Through use of the devices and methods of the eighth embodiment, the wearer can access a variety of applications that are useful in different situations. One example is the ability of the wearer to summon "roadside" assistance through a user interface if there is a fall or mechanical failure of the exoskeleton, at which point a central server is notified to dispatch aid to the exoskeleton location and to convey through the user interface an estimated time of arrival. In another example, the wearer can interact with a virtual physical therapist who assists the wearer in a therapy routine. Data from these therapy sessions is sent to the central server, allowing improvements to be made to the physical therapy regimes prescribed by the physical therapist. Similarly, in a further example, the wearer is able to access various applications related to games that encourage certain physical exercises or improvements in skills associated with exoskeleton use, with these games being downloadable from the central server and running on the exoskeleton control system. In another example, the exoskeleton wearer makes use of a virtual assistant application (such as Siri™ or Cortana™), with queries posed by the wearer being initially processed within the exoskeleton control system. The exoskeleton control system is then able to draw upon additional data from the central server (which can be connected to the broader internet) if needed to fully answer the question or permit other functions, such as reserving a table at a restaurant. In another example, the central server transmits information to an application running on the exoskeleton control system that allows the wearer to receive alerts from the central server, such as news of an impending thunderstorm that prompts the wearer to seek shelter indoors. In another example, the wearer can choose to download specific or customizable user interface dashboards from the central server, with these dashboards then running on the exoskeleton control system and allowing for wearer-selected user interface functions. For example, these functions can include enabling or disabling exoskeleton functionalities or rates of movement based on self-selected exoskeleton wearer skill. Similarly, the wearer can select exoskeleton control system setting modifications from the central server to modify exoskeleton control system settings.

Figure 8B:
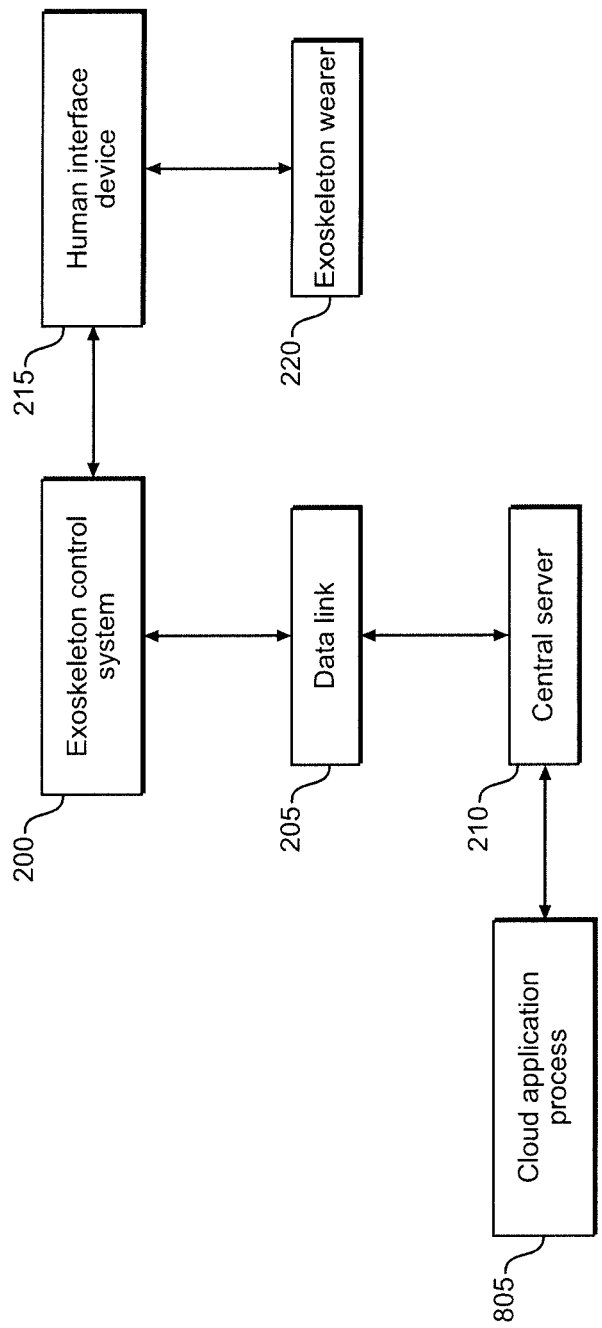
FIG. 8B is a block diagram of the parties communicating in a first variation of the eighth embodiment.

Turning to FIG. 8B, a block diagram shows the parties in communication in a first variation of the eighth embodiment of the present invention. Exoskeleton control system 200 is in communication with data link 205, which is in communication with central server 210. Through data link 205, control system 200 is able to send data to and receive data from central server 210. Control system 200 is also in communication with human interface device 215, which interacts with exoskeleton wearer 220. As a result, wearer 220 can interact with control system 200. Since control system 200 is in communication with central server 210, wearer 220 can also interact, indirectly, with central server 210. A cloud application process 805 runs on central server 210. Wearer 220 is able to interact with cloud application process 805 through human interface device 215, with data being relayed to and from human interface device 215 via control system 200 and data link 205. This embodiment has the advantage, relative to the embodiment shown in FIG. 8A, of allowing for far greater processing power to be used to run certain applications, including applications that are not able to run on exoskeleton control system 200. However, one disadvantage of this arrangement is that an exoskeleton cannot make use of cloud application process 805 without network communication. Accordingly, the communication between control system 200 and central server 210 is preferably constant, although this is not required for all applications.

As an example of the first variation of the eighth embodiment of the present invention, consider a disabled person using an ambulatory exoskeleton for both therapeutic and mobility purposes. Through use of the devices and methods of the first variation of the eighth embodiment, the wearer can access a variety of cloud-based applications that are useful in different situations. For example, a virtual physical therapist application or virtual assistant application process being run on a central server, but accessed by the wearer though a human interface device, can make use of computationally expensive deep learning or cognitive computing analytics in order to better respond to the needs or requests of the wearer (as compared with an application process being run on an exoskeleton control system). Other cloud-based applications can also be made accessible to the wearer, such as social networking applications, exercise or learning games or any of a host of subscription-based software products and applications.

Figure 8C:
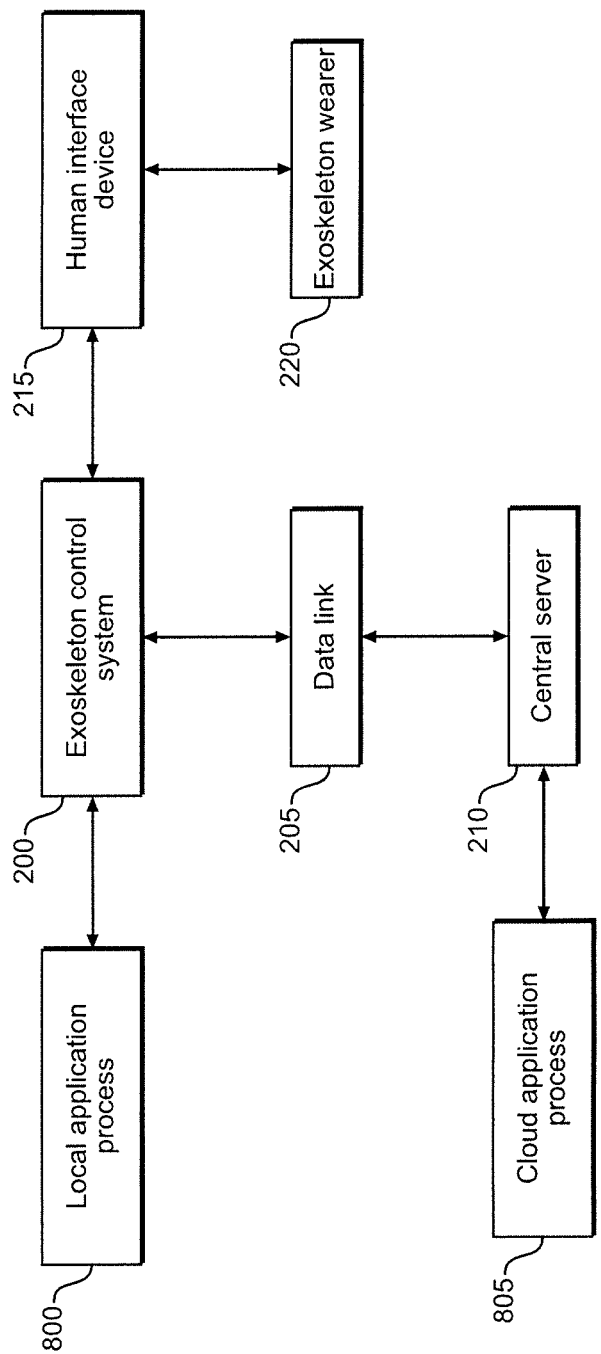
FIG. 8C is a block diagram of the parties communicating in a second variation of the eighth embodiment.

In FIG. 8C, a block diagram shows the parties in communication in a second variation of the eighth embodiment of the present invention. Exoskeleton control system 200 is in communication with data link 205, which is in communication with central server 210. Through data link 205 control system 200 is able to send data to and receive data from central server 210. Control system 200 is also in communication with human interface device 215, which interacts with exoskeleton wearer 220. As a result, wearer 220 can interact with control system 200. Since control system 200 is in communication with central server 210, wearer 200 can also interact, indirectly, with central server 210. Local application process 800 runs on control system 200, while cloud application process 805 runs on central server 210. Local application process 800 and cloud application process 805 are in communication through data link 205. Wearer 220 is able to interact with local application process 800 and cloud application process 805 through human interface device 215, with data being relayed to and from human interface device 215 via control system 200 and data link 205. In some embodiments, local application process 800 is a backup of cloud application process 805, such that at least some application function can be maintained even with intermittent network communication. In some embodiments, cloud application process 805 serves as a backup of local application process 800, such that no data or active processes are lost in the case of a program crash in control system 200. In some embodiments, the communication between control system 200 and central server 210 is constant. In other embodiments, the communication between control system 200 and central server 210 is intermittent, with local application process 800 allowing wearer 200 to still access an application if communication to central server 210 is disrupted.

As an example of the second variation of the eighth embodiment of the present invention, consider a disabled person using an ambulatory exoskeleton for both therapeutic and mobility purposes. Through use of the devices and methods of the second variation of the eighth embodiment, the wearer can run a largely cloud-based application, taking advantage of the superior processing capabilities of a central server, while maintaining some application function even if he or she chooses to move in and out of areas, such as tunnels or other structures, with little or no network connectivity.

Figure 9:
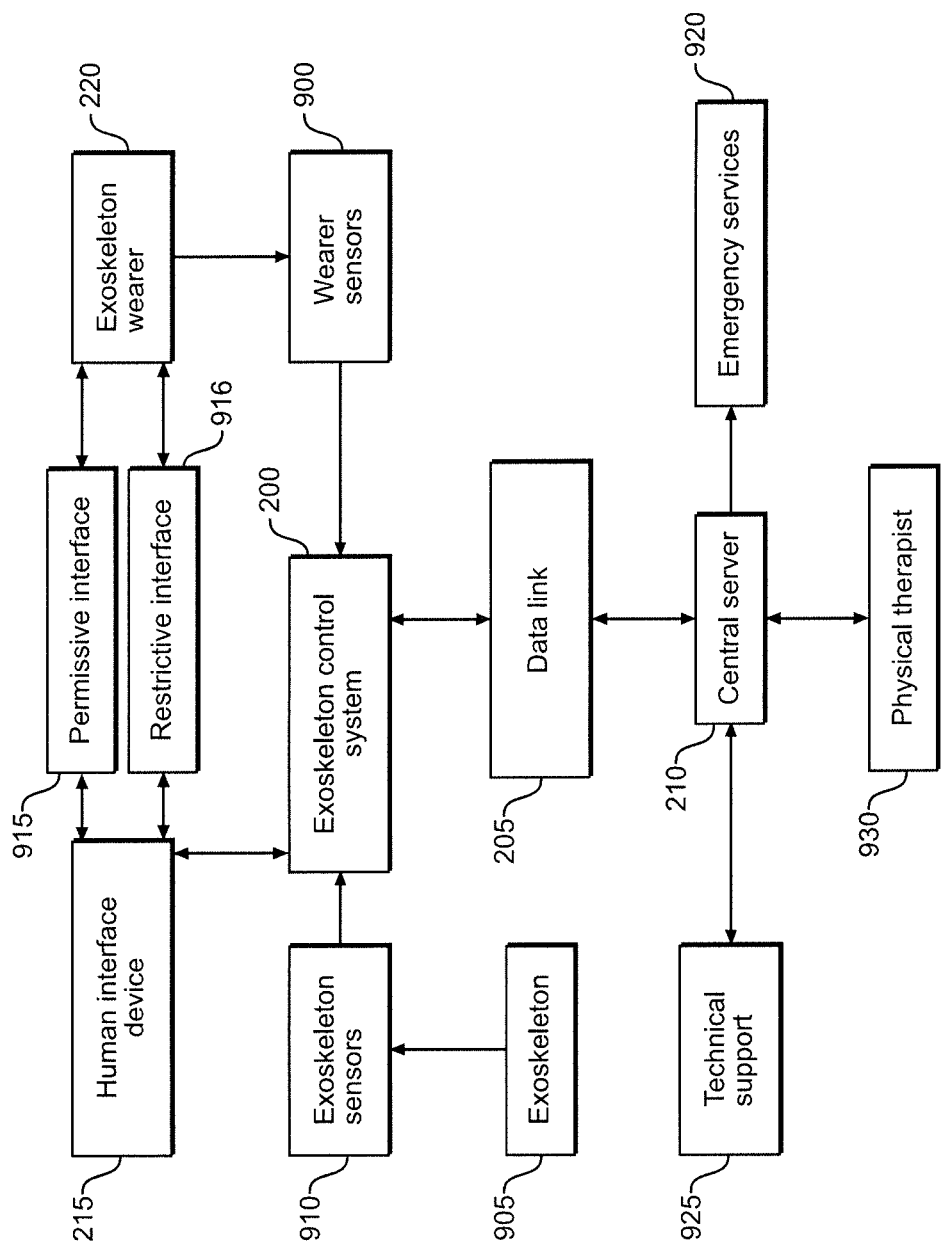
FIG. 9 is a block diagram of the parties communicating in a ninth embodiment of the present invention.

As discussed above in connection with the fifth embodiment, an ambulatory exoskeleton can, based on configuration and sensors present, provide a substantial amount of information about a wearer's performance and state. Similar to the fifth embodiment, a ninth embodiment of the present invention provides ways by which an exoskeleton control system can serve as a basis for a local network or "body area network". The "body area network" is in communication with a central server in order to allow remote monitoring and analytic functions. Also, the central server can enable or disable certain exoskeleton features or initiate technical, medical or emergency support in response to the data received. The ninth embodiment is illustrated in FIG. 9. Exoskeleton control system 200 is in communication with central server 210 through data link 205. Control system 200 receives information on the state and/or performance of exoskeleton wearer 220 from wearer sensors 900 and information on the state and/or environment of an exoskeleton 905 from exoskeleton sensors 910. Control system 200 is in communication with human interface device 215, with control system 200 selectively activating either a permissive interface 915 or a restrictive interface 916 on human interface device 215. Wearer 220 interacts with human interface device 215 using whichever interface is activated by control system 200. Sensor data received by control system 200 is transmitted, either continuously or intermittently, to central server 210, which performs various analyses on this data. Central server 210 is able to initiate different actions in response to these data analyses, such as summoning of emergency services 920, placing control system 200 and wearer 220 in contact with either technical support 925 or a physical therapist 930 or commanding control system 200 to toggle human interface device 215 between permissive interface 915 and restrictive interface 916. In some embodiments, there are more than two interface settings. In some embodiments, wearer sensors 900 include but are not limited to EEG, EMG or EKG sensors or sensors that measure pulse, blood pressure, blood glucose or body temperature. In some embodiments, exoskeleton sensors 910 measure exoskeleton or environmental state features including but not limited to joint angle, applied actuator forces, pressure on wearer 200, pressure on a support surface, environmental temperature, proximity to objects or surfaces or geographical position using any of a variety of sensor devices known in the art.

As an example of the ninth embodiment of the present invention, consider an exoskeleton being used in the home for mobility and rehabilitation purposes by a severely disabled elderly person. The exoskeleton, which makes use of the devices and methods of the ninth embodiment, can be set in the restrictive interface mode for mobility purposes due to the level of disability of the wearer, thereby limiting the speed of some motions, e.g., restricting movements to walking rather than running. In the event of a fall or medical emergency such as a stroke or heart attack, a central server can detect this event and automatically summon emergency services. In this example, the exoskeleton is also being used by the wearer for rehabilitation functions, at which time the wearer is in communication with a remote physical therapist via the central server. During physical therapy sessions, the physical therapist is able to command the exoskeleton control system to change to the permissive interface mode, allowing the wearer additional functionalities while under the supervision of the physical therapist. For exoskeleton wearers with a disability resulting in loss of sensation in some part of the body, the ninth embodiment can also be used for early detection of pressure sores directly or due to changes in gait. Additionally, pressure mapping can be used to adjust the position of the exoskeleton for improved user comfort. Furthermore, wearer sensors can be used to effect the application of anti-inflammatory, analgesic, glucose regulating or other medication in response to sensor data.

As an additional example of the ninth embodiment, consider an exoskeleton being used in a physical therapy clinic environment, where multiple patients wear the exoskeleton over the course of a week. Through use of the devices and methods of the ninth embodiment, exoskeletons equipped with various sensors can be used to identify specific users based on wearer biometrics, gait characteristics or other unique markers. A connection to a central server through a two-way data link allows for identification of users new to a particular exoskeleton, such that centralized settings for exoskeletons and user interfaces can be automatically applied. In such a therapeutic setting, the exoskeleton and sensors in combination with central server communication can be used for automatic range of motion tests for each patient with remote monitoring or even to monitor and adjust the course of physical therapy over multiple sessions.

As yet another example of the ninth embodiment, consider an industrial exoskeleton being used by a construction worker. As discussed above in connection with the fourth embodiment, it is generally desirable to determine when an exoskeleton will need service so that service can occur before a failure. Through use of the devices and methods of the ninth embodiment, the industrial exoskeleton's state and usage can be monitored by a central server, triggering automatic or analytics-dependent maintenance alerts. In some embodiments, the exoskeleton can be programmed to disallow further use (or specific types of use) through a change from a permissive to a restrictive user interface setting until required maintenance is completed. Specific uses can be disallowed in certain weather conditions, such as heavy rain, or after a fall or other event that may have damaged the exoskeleton or injured the wearer. In some embodiments, this feature lockout can be overridden by the wearer, optionally after a warning, since this can be of advantage in an emergency situation where disabling the exoskeleton could put human life at risk. In some embodiments, the exoskeleton sensors can be used to detect a workplace injury and automatically summon emergency medical services.

Figure 10:
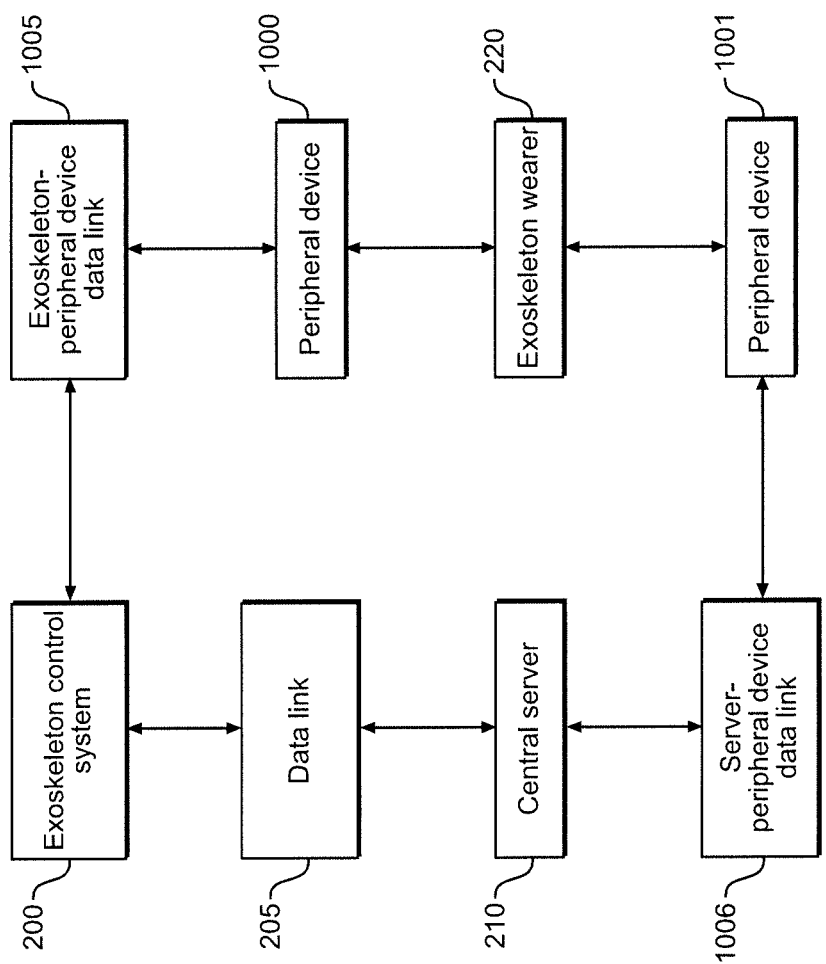
FIG. 10 is a block diagram of the parties communicating in a tenth embodiment of the present invention.

As discussed in connection with the sixth embodiment, an exoskeleton can be networked with peripheral devices. A tenth embodiment of the present invention expands on this idea and is illustrated in FIG. 10. In FIG. 10, exoskeleton wearer 220, who is not presently wearing an exoskeleton, is able to communicate with both exoskeleton control system 200 and central server 210 through the use of peripheral devices. This allows wearer 220 to issue commands to control system 200 or remotely access data stored on either control system 200 or central server 210. Wearer 220 can interact with a peripheral device 1000, which is in communication with control system 200 through an exoskeleton-peripheral device data link 1005, or a peripheral device 1001, which is in communication with control system 200 through central server-peripheral device data link 1006. As in prior embodiments, central server 210 is networked with control system 200 through data link 205. In some embodiments, a single peripheral device is able to interact with control system 200 or central server 210 through either of data links 1005 and 1006. In some embodiments, one or both of peripheral devices 1000 and 1001 contain various sensors. In some embodiments, one or both of peripheral devices 1000 and 1001 are capable of interacting with additional networks, such as Wi-Fi networks or cellular internet.

As an example of the tenth embodiment of the present invention, consider a disabled person using an exoskeleton for mobility purposes. By making use of the devices and methods of the tenth embodiment, the person can network his or her smartphone with the exoskeleton control system, granting the exoskeleton control system access to data from smartphone sensors, such a GPS or other location services. As an additional example of the tenth embodiment, consider a disabled person using an ambulatory exoskeleton for mobility in a public place. Through use of the devices and methods of the tenth embodiment, the person can command his or her exoskeleton to detect the peripheral devices of nearby people and modify its walking speed to match the pace of the crowd for better walking in a crowded community environment. Similarly, multiple exoskeletons can communicate so as to allow them to tightly match pacing and maneuvering using swarm walking, which allows for more exoskeletons to walk in a tighter space without colliding. As a further example of the tenth embodiment, consider a disabled person who uses both a wheelchair and an ambulatory exoskeleton for mobility purposes. Through use of the devices and methods of the tenth embodiment, the person can use a smartphone to cause his or her exoskeleton to walk to him or her or to a charging station. In another embodiment, a semi-public exoskeleton sharing service can have a web or smartphone application that allows a disabled person to rent an exoskeleton for a certain period of time and summon the exoskeleton to his or her location.

Figure 11A:
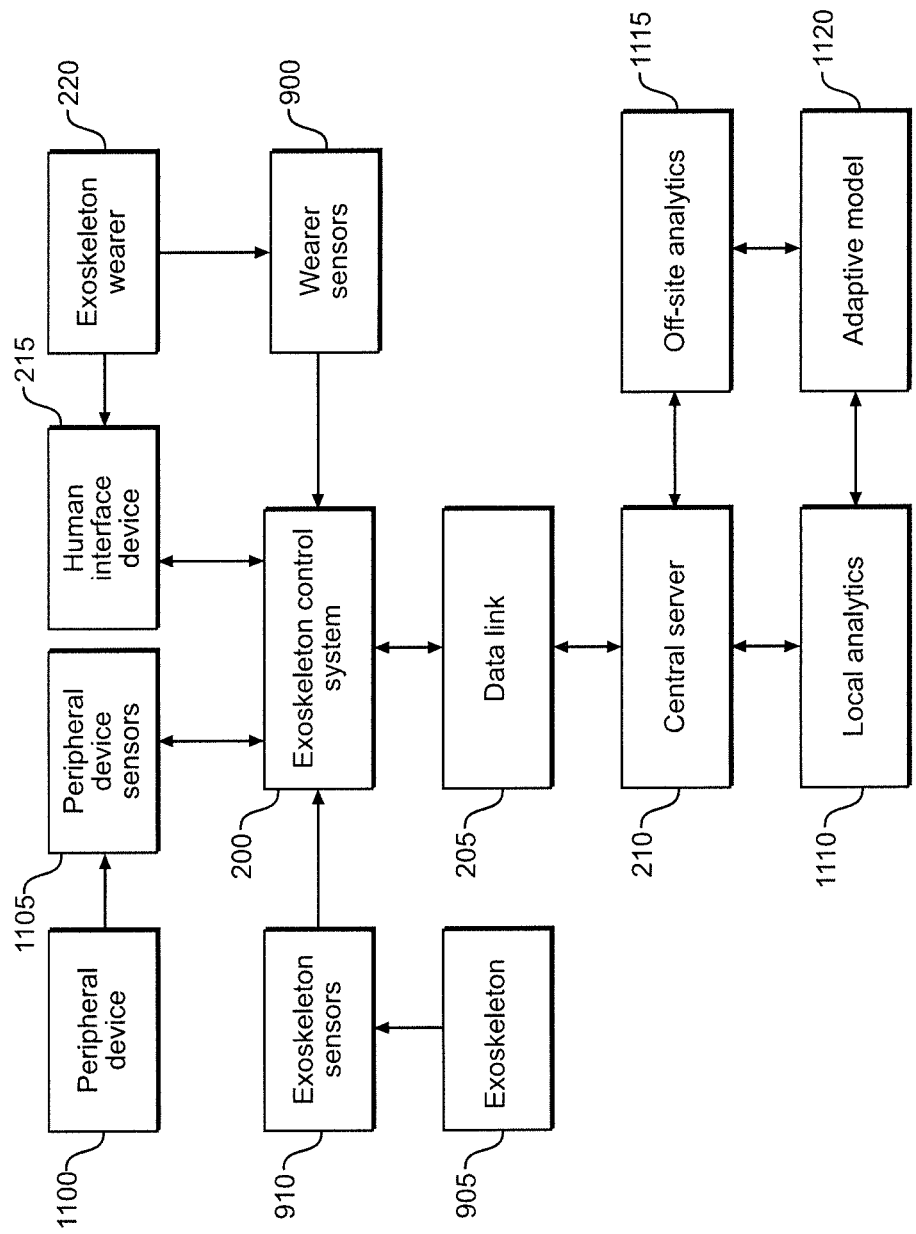
FIG. 11A is a block diagram of the parties communicating in an eleventh embodiment of the present invention.
Figure 11B:
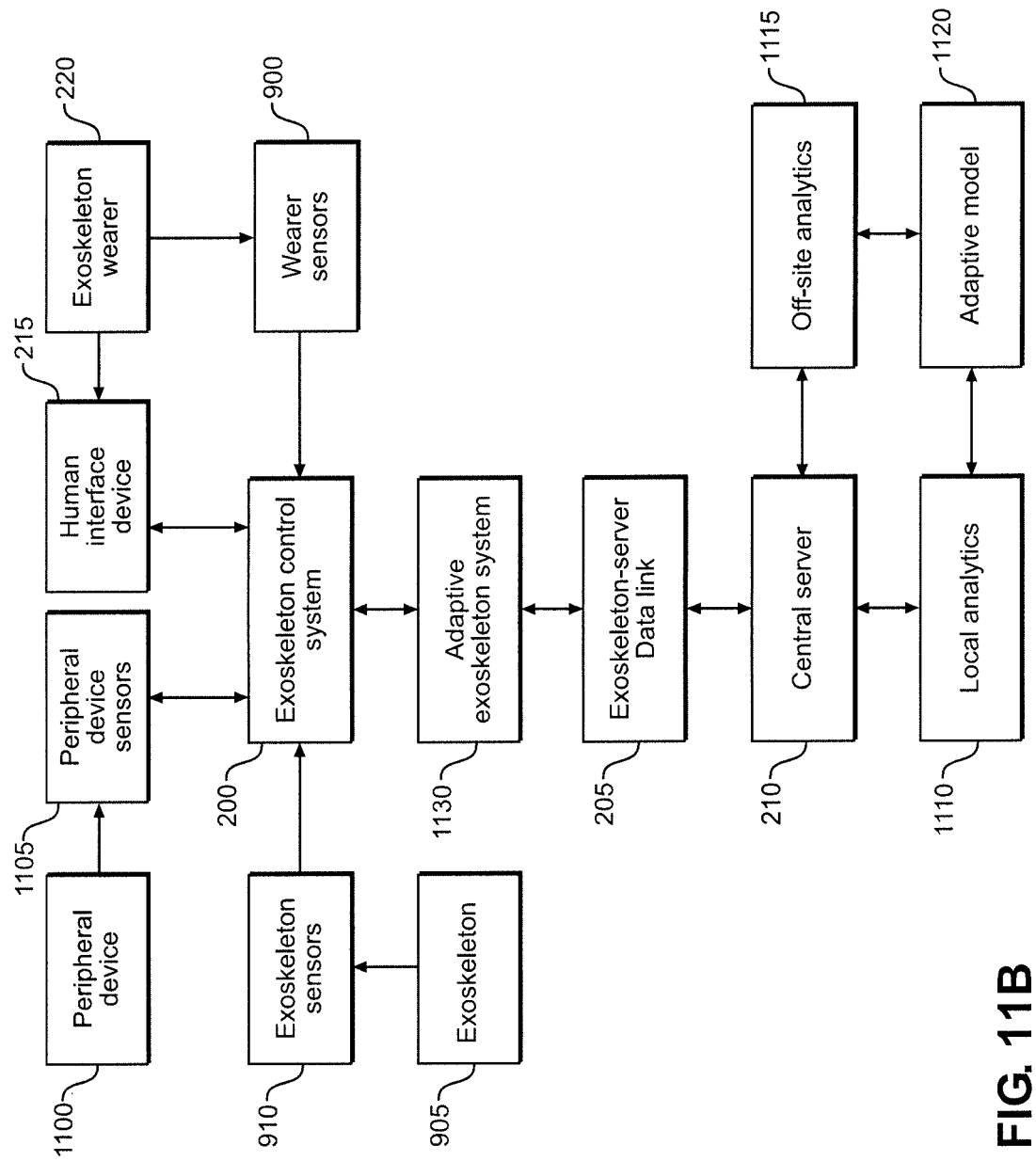
FIG. 11B is a block diagram of the parties communicating in a variation of the eleventh embodiment.

As in the seventh embodiment of the present invention, an eleventh embodiment involves a central server that performs data analytics tasks using data provided by the control systems of a deployed fleet of exoskeletons. The data includes linked and unlinked datasets on exoskeleton location and movement, power usage in various tasks, wearer performance in a variety of maneuvers, body sensor data and/or peripheral device data. These datasets provide a wealth of information that can be sorted and analyzed using techniques such as big data analytics, deep learning, cognitive computing and neuromorphic computing. This analysis facilitates improvements to exoskeleton design, physical therapy routines, responses to failures, navigation from point-to-point and a host of other functions of use to exoskeleton designers or wearers. The eleventh embodiment is shown in FIGS. 11A and 11B. In FIG. 11A, exoskeleton control system 200 is in communication with and receives data about the state of exoskeleton 905, a peripheral device 1100 and exoskeleton wearer 220 from exoskeleton sensors 910, peripheral device sensors 1105, wearer sensors 900 and human interface device 215. Control system 200 then transmits this data to central server 210 using data link 205, with central server 210 performing local analytics 1110 and/or off-site analytics 1115 (e.g., outsourced to a specialist analytics entity) to develop an adaptive model 1120. In some embodiments, the model is not adaptive, and data is recompiled and analyzed to make a new model periodically. In other embodiments, the model is changed incrementally as new data is collected. In some embodiments, data from many exoskeleton control systems are collected to build and/or adjust the model.

Turning to FIG. 11B, a first variation of the eleventh embodiment is shown. As with the embodiment of FIG. 11A, control system 200 is in communication with and receives data about the state of exoskeleton 905, peripheral device 1100 and exoskeleton wearer 220 from exoskeleton sensors 910, peripheral device sensors 1105, wearer sensors 900 and human interface device 215. Control system 200 has an adaptive exoskeleton system 1130, which is affected by and to some extent processes the data received by control system 200. Adaptive exoskeleton system 1130 then transmits this data to central server 210 using data link 205, with central server 210 performing local analytics 1110 and/or off-site analytics 1115 (e.g., outsourced to a specialist analytics entity) to develop adaptive model 1120. In some embodiments, adaptive exoskeleton system 1130 is an adaptive algorithm. In some embodiments, adaptive exoskeleton system 1130 contains an adaptive hardware element, including selectively switchable elements such as a field programmable gate array (FPGA), or memristive components that are physically changed in terms of conductivity or other characteristics as a result of certain processes. In some embodiments, central server 210 monitors the changes in adaptive exoskeleton system 1130. In some embodiments, central server 210 is able to imprint a copy of adaptive exoskeleton system 1130 from one exoskeleton into another exoskeleton.

As an example of the eleventh embodiment of the present invention, consider a server that is in communication with hundreds of exoskeletons that are being used in clinical therapy settings. Through use of the eleventh embodiment, the data accumulated from the control systems of these exoskeletons and relayed to the server via data links can be used to determine optimal points to recharge or discharge batteries in order to provide for maximum battery life. New instructions are then relayed from the server to the exoskeleton control systems, and optionally through human interface devices to exoskeleton wearers, relating to the determined best use parameters for the exoskeletons in terms of maximizing battery life. Similarly, the analysis of data received from wearer sensors of these exoskeletons can be used to compare distinct physical therapy regimes and outcomes over a large population of patients. Deep learning can be used to analyze massive datasets in order to determine unexpected or unpredicted correlations amongst a broad group of datasets from the larger exoskeleton fleet.

As an additional example of the eleventh embodiment, consider one disabled person using a personal exoskeleton for mobility and physical therapy purposes. While the person can benefit from the bulk analytics of the greater exoskeleton fleet, additional benefits can be gained through the inclusion of an adaptive component in his or her exoskeleton that is trained specifically for his or her needs. This adaptive element is teachable and trainable through direct interaction with the exoskeleton wearer and/or his or her physical therapist. Examples of trainable adaptive robotics have recently been discussed in both academic and non-academic publications. These adaptive systems can make use of deep learning processes or learning algorithms or, in a preferred embodiment, contain one or more adaptive hardware systems, as substantial power consumption advantages can be realized through use of adaptive hardware (as compared with systems without adaptive hardware components). These local adaptive systems can aid in improving exoskeleton trajectories for certain motions or personalizing the exoskeleton function in other ways that are of use to a specific exoskeleton wearer.

Based on the above, it should be readily apparent that the present invention provides devices and methods that allow for two-way communication between an exoskeleton control system and a central system. An exoskeleton wearer is able to make use of the communication linkage for applications that increase the usefulness of the exoskeleton to the wearer. The central server is able to make use of the communication linkage for analytic functions that are of value to the wearer or a central server operator. In addition, peripheral devices can communicate with and be networked to the control system and the central server. In general, the present invention involves collecting first data with a first exoskeleton and transmitting the first data from the first exoskeleton to a central server or a peripheral device. Second data is generated using the first data, and the second data is transmitted from the central server or the peripheral device to the first exoskeleton or a second exoskeleton. Although described with reference to preferred embodiments, it should be readily understood that various changes or modifications could be made to the invention without departing from the spirit thereof. In general, the invention is only intended to be limited by the scope of the following claims.

The invention claimed is:

1. A method of communication between a first exoskeleton and a central server or a peripheral device, the method comprising:
   collecting first data with the first exoskeleton;
   transmitting the first data from the first exoskeleton to the central server or the peripheral device;
   generating second data using the first data; and
   transmitting the second data from the central server or the peripheral device to the first exoskeleton or a second exoskeleton,
wherein collecting the first data includes collecting data about a wearer of the first exoskeleton, and transmitting the first data includes transmitting the first data from the first exoskeleton to the central server, the method further comprising:
   determining whether the wearer is a known wearer or a new wearer based on the first data; and
   applying wearer specific settings to the first exoskeleton if the wearer is a known wearer.

2. The method of claim 1, wherein an amount of the first data collected with and transmitted from the first exoskeleton varies depending on a movement being performed by the first exoskeleton during collection, and wherein:
   1) the amount of the first data collected with and transmitted from the first exoskeleton varies depending on a speed of the movement being performed by the first exoskeleton; or
   2) the amount of the first data collected with and transmitted from the first exoskeleton varies depending on a complexity of the movement being performed by the first exoskeleton.

3. The method of claim 2, wherein the amount of first data collected with and transmitted from the first exoskeleton increases when a fall is occurring or likely to occur.

4. The method of claim 1, wherein transmitting the second data includes transmitting the second data from the peripheral device to the first exoskeleton, the method further comprising adjusting a movement speed or direction of the first exoskeleton based on the second data, wherein transmitting the second data from the peripheral device to the first exoskeleton includes transmitting the second data from a peripheral device belonging to a person other than a wearer of the first exoskeleton, and wherein:
   1) adjusting the movement speed or direction of the first exoskeleton includes adjusting the movement speed or direction of the first exoskeleton based on a movement speed or direction of the person; or
   2) the peripheral device is another exoskeleton.

5. The method of claim 1, wherein transmitting the second data includes transmitting the second data from the peripheral device to the first exoskeleton, the method further comprising transmitting the second data from the first exoskeleton to the central server.

6. The method of claim 5, further comprising displaying the second data to a wearer of the first exoskeleton.

7. The method of claim 5, wherein the peripheral device constitutes a first peripheral device, the method further comprising:
   transmitting third data from a second peripheral device to a third exoskeleton;
   transmitting the third data from the third exoskeleton to the central server; and
   displaying the second and third data to a person other than a wearer of the first or third exoskeletons, and wherein:
   the first and second peripheral devices are weapons;
   the first exoskeleton is worn by a first soldier;
   the third exoskeleton is worn by a second soldier; and
   displaying the second and third data includes displaying the second and third data to a commander of the first and second soldiers.

8. A method of communication between a first exoskeleton and a central server or a peripheral device, the method comprising:
   collecting first data with the first exoskeleton;
   transmitting the first data from the first exoskeleton to the central server or the peripheral device;
   generating second data using the first data; and
   transmitting the second data from the central server or the peripheral device to the first exoskeleton or a second exoskeleton,
wherein an amount of the first data collected with and transmitted from the first exoskeleton varies depending on a movement being performed by the first exoskeleton during collection, and wherein:
   1) the amount of the first data collected with and transmitted from the first exoskeleton varies depending on a speed of the movement being performed by the first exoskeleton; or
   2) the amount of the first data collected with and transmitted from the first exoskeleton varies depending on a complexity of the movement being performed by the first exoskeleton, and
wherein the amount of the first data collected with and transmitted from the first exoskeleton is greater when the first exoskeleton is worn by a wearer than when the first exoskeleton is not worn, greater when the wearer is standing than when the wearer is sitting, greater when the wearer is walking than when the wearer is standing and greater when the wearer stands up or sits down than when the wearer is walking, and wherein the amount of the first data collected with and transmitted from the first exoskeleton increases with increased wearer walking speed.

9. The method of claim 1, the method further comprising: modifying movement of the first exoskeleton in real time based on the first data, and wherein:
   1) modifying the movement of the first exoskeleton includes providing additional assistance to the wearer if the data indicates that the wearer is fatigued; or
   2) modifying the movement of the first exoskeleton includes providing reduced assistance to the wearer or increasing movement speed of the first exoskeleton if the data indicates that a heart rate of the wearer is not sufficiently elevated.

10. The method of claim 1, wherein:
   1) collecting the first data includes collecting data about the wearer with sensors to create sensor data, and determining whether the wearer is a known wearer or a new wearer includes determining whether the wearer is a known wearer or a new wearer based on the sensor data; or
   2) collecting the data includes collecting data about a gait of the wearer to create gait data, and determining whether the wearer is a known wearer or a new wearer includes determining whether the wearer is a known wearer or a new wearer based on the gait data.

11. The method of claim 1, further comprising:
running a first copy of an application on a control system of the first exoskeleton; and
running a second copy of the application on the central server; and further comprising:
   1) controlling the first exoskeleton based on the second copy of the application when the first exoskeleton is in communication with the central server, and controlling the first exoskeleton based on the first copy of the application when the first exoskeleton is not in communication with the central server; or
   2) controlling the first exoskeleton based on the first copy of the application, and controlling the first exoskeleton based on the second copy of the application if the first copy of the application crashes.

12. The method of claim 1, further comprising:
causing the first exoskeleton to enter a restricted mode in which the first exoskeleton is prevented from performing at least some movements, movement speed of the first exoskeleton is limited or movement complexity of the first exoskeleton is limited, wherein causing the first exoskeleton to enter the restricted mode includes:
   1) causing the first exoskeleton to enter the restricted mode based on a level of disability of a wearer of the first exoskeleton;
   2) causing the first exoskeleton to enter the restricted mode based on an environment in which the first exoskeleton is being operated;
   3) causing the first exoskeleton to enter the restricted mode based on maintenance needs of the first exoskeleton; or
   4) causing the first exoskeleton to enter the restricted mode in response to a fall of the first exoskeleton.

13. The method of claim 1, wherein transmitting the first data includes transmitting the first data from the first exoskeleton to the central server, the method further comprising:
collecting third data with a third exoskeleton;
transmitting the third data from the third exoskeleton to the central server;
analyzing the first data and the third data to identify which physical therapy routines or failure responses are most effective or which exoskeleton parts should be redesigned for greater durability.

14. The method of claim 8, wherein collecting the first data includes collecting data about a wearer of the first exoskeleton, and transmitting the first data includes transmitting the first data from the first exoskeleton to the central server, the method further comprising:
determining whether the wearer is a known wearer or a new wearer based on the first data; and
applying wearer specific settings to the first exoskeleton if the wearer is a known wearer.

15. A system of communication comprising:
a first exoskeleton configured to collect first data about a wearer of the first exoskeleton and transmit the first data; and
a central server or a peripheral device configured to receive the first data transmitted from the first exoskeleton, generate second data using the first data, with the second data including whether the wearer is a known wearer or a new wearer, and transmit the second data to the first exoskeleton or a second exoskeleton while applying wearer specific settings to the first or second exoskeleton if the wearer is a known wearer.

16. The system of claim 15, wherein the first exoskeleton is configured such than an amount of the first data collected and transmitted varies depending on a movement being performed by the first exoskeleton during collection.

17. The system of claim 15, wherein:
the system comprises the peripheral device; and
the peripheral device is configured to transmit the second data to the first exoskeleton, and wherein:
   1) the first exoskeleton is configured to adjust a movement speed or direction of the first exoskeleton based on the second data; or
   2) the first exoskeleton is configured to transmit the second data to a central server.

18. The system of claim 15, wherein:
the first exoskeleton is configured to modify movement of the first exoskeleton in real time based on the first data.

19. The system of claim 15, wherein:
the system comprises the central server;
the first exoskeleton is configured to run a first copy of an application on a control system of the first exoskeleton; and
the central server is configured to run a second copy of the application on the central server.

20. The system of claim 15, further comprising a third exoskeleton configured to collect and transmit third data, wherein:
the system comprises the central server;
the central server is configured to:
   receive the third data transmitted from the third exoskeleton; and
   analyze the first data and the third data to identify which physical therapy routines or failure responses are most effective or which exoskeleton parts should be redesigned for greater durability.

* * * * *